(12) United States Patent
Tang et al.

(10) Patent No.: US 8,299,069 B2
(45) Date of Patent: Oct. 30, 2012

(54) 2-(2-OXOINDOLINE-3-YLIDENE)METHYL-5-(2-HYDROXY-3-MORPHOLIN-4-YL-PROPYL)-6,7-DIHYDRO-1H-PYRROL[3,2-C]PYRIDINE-4(5H)-ONE COMPOUNDS AND USE AS PROTEIN KINASE INHIBITORS

(75) Inventors: Peng Cho Tang, Shanghai (CN); Jialiang Yang, Shanghai (CN); Yidong Su, Shanghai (CN); Fuqiang Zhao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 257 days.

(21) Appl. No.: 12/733,193

(22) PCT Filed: Jul. 29, 2008

(86) PCT No.: PCT/CN2008/001388
§ 371 (c)(1),
(2), (4) Date: Feb. 12, 2010

(87) PCT Pub. No.: WO2009/024016
PCT Pub. Date: Feb. 26, 2009

(65) Prior Publication Data
US 2010/0160317 A1    Jun. 24, 2010

(30) Foreign Application Priority Data
Aug. 15, 2007    (CN) .......................... 2007 1 0141874

(51) Int. Cl.
C07D 413/14    (2006.01)
A61K 31/5377   (2006.01)
(52) U.S. Cl. ..................... 514/234.5; 544/127
(58) Field of Classification Search .................. None
See application file for complete search history.

(56) References Cited

U.S. PATENT DOCUMENTS
6,465,507 B2    10/2002   Tang
7,053,086 B2     5/2006   Tang
2004/0209937 A1 10/2004   Murray et al.

FOREIGN PATENT DOCUMENTS
WO    WO01/94312 A2     12/2001
WO    WO2007/085188 A1   8/2007

OTHER PUBLICATIONS

Grant & Hackh's Chemical Dictionary (5th Ed. 1987) at p. 148.*
Hanks and Hunter, 1995, FASEB J., 9:7576-596.
Cadena and Gill, 1992, FASEB J., 6:2332-2337.
Schlessinger and Ullrich, 1992, Neuron, 9:383-391.
Vandergeer et al.,1994, Annu. Rev. Cell Biol., 10;251-337.
Chiao et al., 1990, Cancer Metast. Rev.,9:63-80.
Hunter, 1991,Cell, 64:249-270.
Ferrara N et al.,Endocr Rev., 1997, 18,4-25.
Torimura T et al.,Hum Pathol., 1998, 29, 986-991.
Li Ling et al., Acta Biochimica et Biophysica Sinica,2002,34(1),21-27.
Ellis LM et al.,J Biol Chem 1998, 273, 1052-1057.
Gordon et al.,Proc Am Soc Clin Oncol, 1998, 17,211a.

* cited by examiner

*Primary Examiner* — Michael Barker
(74) *Attorney, Agent, or Firm* — Hedman & Costigan, P.C.; James V. Costigan

(57) ABSTRACT

Pyrrolo[3,2-c]pyridine-4-one-2-indolinone compounds, especially 2-(2-oxoindoline-3-ylidene)methyl-5-(2-hydroxy-3-morpholin-4-yl-propyl)-6,7-dihydro-1H-pyrrol[3,2-c]pyridine-4(5H)-one compounds. Their preparation and pharmaceutical composition, and pharmaceutical use as protein kinase inhibitors.

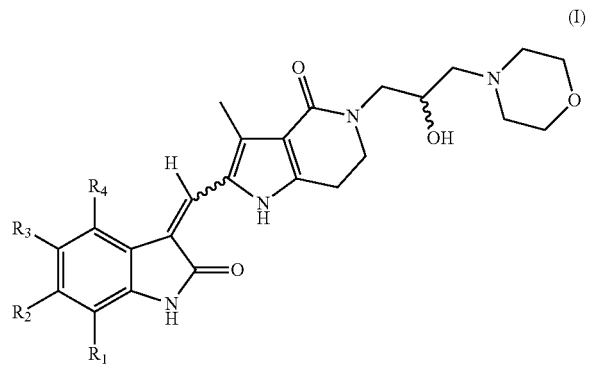

(I)

11 Claims, No Drawings

2-(2-OXOINDOLINE-3-YLIDENE)METHYL-5-(2-HYDROXY-3-MORPHOLIN-4-YL-PROPYL)-6,7-DIHYDRO-1H-PYRROL[3,2-C]PYRIDINE-4(5H)-ONE COMPOUNDS AND USE AS PROTEIN KINASE INHIBITORS

FIELD OF THE INVENTION

This invention relates to a series of new pyrrolofused six-membered aza-hetero cyclic hydroxyl morphine derivatives, especially novel 2-(2-oxo indoline-3-ylidene)methyl-5-(2-hydroxyl-3-morphine-4-yl-propyl)-6,7-dihydro-1H-pyrrol[3,2-c]pyridine-4(5H)-one derivatives, the preparation thereof, pharmaceutical compositions containing such derivatives and the use of such derivatives as therapeutic agents, especially as protein kinase inhibitors.

BACKGROUND OF THE INVENTION

Cellular signal transduction is a fundamental mechanism whereby extracellular stimuli are relayed to the interior of cells and subsequently regulate diverse cellular, processes. These signals regulate a wide variety of physical responses in the cell including proliferation, differentiation, apoptosis and motility. The extracellular signals take the form of a diverse variety of soluble factors including growth factors as well as paracrine, autocrine and endocrine factors. By binding to specific transmembrane receptors, growth factor ligands communicate extracellular signals to the intracellular signalling pathways, thereby causing the individual cell to respond to extracellular signals. Many of these signal transduction processes utilize the reversible process of the phosphorylation of proteins involving specific protein kinases and phosphatases.

Protein kinases (PKs) play a critical role in the signal transduction process. It transfers the gamma phosphate group from ATP to specific amino acid residue in a functional protein, resulting in a series of biological responses. Protein kinases are classified into two groups, according to amino acid specificity as substrate in the process of the phosphorylation: serine/threonine kinases (STKs) and protein tyrosine kinases (PTKs).

The mechanism of tyrosine phosphorylation widely exists in the signal transduction process, and controls several cell functions such as mitosis, cell cycle progression and differentiation, etc.(Hanks and Hunter, 1995, FASEB J. 9:576-596; Cadena and Gill, 1992, FASEB J. 6:2332-2337; Schlessinger and Ullrich, 1992, Neuron 9:383-391; Vandergeer et al., 1994, Arum. Rev. Cell Biol. 10:251-337). Mutation, uncontrolled or abnormally high level expression of the protein tyrosine kinases have been shown to lead to the conversion of normal cell to neoplastic phenotype(Chiao et al., 1994, Cancer Metast. Rev. 9:63-80; Hunter, 1991, Cell 64:249-270).

Vascular endothelial growth factor (VEGF) was identified as aspecific growth factor acting on vascular endothelial cell, and has been found to have various functions such as stimulating proliferation of endothelial cells, increasing microvascular permeability and inducing angiogenesis (Hanks and Hunter, 1995, FASEB J. 9:576-596). VEGF is known to be the most effective and directly acting angiogenic protein. It is a diffusible endothelial cell-specific mitogen and vascular growth factor (Ferrara N et al., EndocrRev, 1997, 18, 4-25; Tofimura T et al., Hum Pharthol, 1998, 29, 986-991). The VEGF family currently includes six known members: VEGF-A, VEGF-B, VEGF-C, VEGF-D, VEGF-E, and placental growth factor (PDF), which are all forms of dimeric glycoprotein. All VEGF family members contain characteristic regularly spaced eight-cysteine residues referred to as the "cysteine knot" motif. Li ling et al. (Li ling et al., Acta Biochimica et Biophysica Sinica, 2002, 34(1), 21-27) revealed high VEGF expression in malignant tumor cells as well as the high expression of Flk-1, which implicates the existence of both autocrine and paracrine VEGF loops within the tumor. VEGF expression is clearly correlated with intra-tumoral microvessel density, and the VEGF concentration in tissues is correlated with prognosis of solid tumor such as breast cancer, lung cancer, prostate cancer and colon cancer. It is known that hypoxia plays a critical role in stimulating VEGF expression. In addition to the enhancement of gene transcription rate, hypoxia inducing VEGF gene expression in the tumour cell also promotes the stabilization of VEGF mRNA. Three different members that belong to the VEGFR family have been identified: VEGFR-1/Flt-1, VEGFR-2/Flk-1/KDR, and VEGFR-4/Flt-4. VEGFR-1 and VEGFR-2 belong to cell surface tyrosine kinase receptors whose expression is mainly restricted to tumor vascular endothelial cells. Vascular endothelium growth factor (VEGF) and vascular endothelial growth factor receptor (VEGFR) play an important role in the process of tumor angiogenesis and has been validated as an important target for anti-cancer biotherapy.

Five strategies targeting the VEGF and VEGFR for anti-tumor therapy will be discussed as follows: 1. Gene therapy (Ellis L M et al. J Biol Chem 1998, 273, 1052-1057): VEGF and VEGFR have been implicated in positive regulation of the tumor angiogenesis. Gene therapy reduces VEGFNEGFR expression or disrupts the signal transduction pathways to inhibit their biological activities. 2. Anti-VEGFNEGFR monoclonal antibodies (Gordon M et al. Proc Am Soc Clin Oneol, 1998, 17, 2IIa): monoclonal antibodies against VEGFNEGFR block the secreted VEGF and VEGFR, and disrupt intracellular VEGF signal transduction to inhibit angiogenesis. 3. Small-molecule inhibitors: the series of su compounds developed by Sugen. 4. Soluble VEGFR: it binds with VEGF, but has no function of signal transduction. 5. Directed therapy: the two main VEGF receptors of Flt-1 and Flk-1/KDR overexpress in tumor vascular endothelial cell, but cannot be dected in adjoining normal tissue vascular endothelium. Hence, VEGF and VEGFR provide the specific target for tumor-directed therapy. VEGF can be combined with other anti-tumor agents, toxins, radionuclides for tumor-directed therapy.

Based on the tyrosine kinase inhibitor SU-14813 and the effective anticancer agent of pyrrolofused six-membered aza-heterocyclic derivatives A, the present invention is directed to design the analogues of formula (I). The compounds of the invention have obvious structure differences with the existing compounds in prior art, and they also show more efficiency and more function.

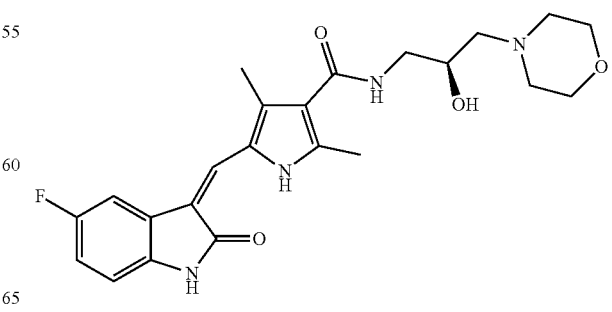

SU-14813

-continued

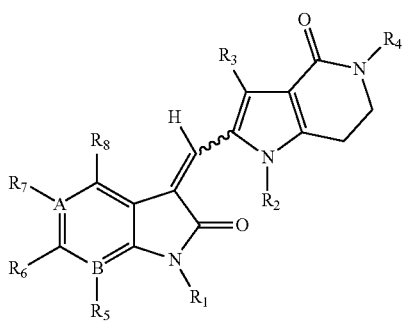

SUMMARY OF THE INVENTION

The present invention is directed to certain compounds of pyrrolofused six-membered aza-heterocyclic hydroxyl morpholine derivatives having formula (I), especially novel protein tyrosine, kinase inhibitors 2-(2-oxoindoline-3-ylidene)methyl-5-(2-hydroxyl-3-morphine-4-yl-propyl)-6,7-dihydro-1H-pyrrol[3,2-c]pyridine-4(5H)-one compounds, their tautomers, enantiomers, the physiologically acceptable salts, metabolites, metabolite prodrugs and their activities in regulating protein kinases activities.

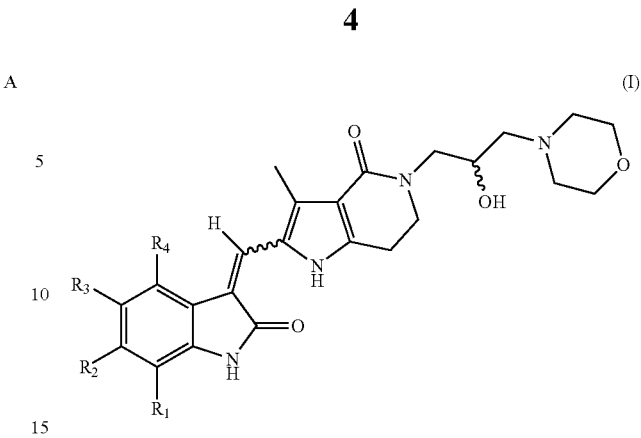

Wherein:

$R_1$, $R_2$, $R_3$, $R_4$ are each independently selected from the group consisting of hydrogen, halogen, alkyl, aryl, heteroaryl, —$OR_5$, —$O[CH_2CH_2O]_rR_7$, —$NR_5R_6$, —$COR_5$ and —$NR_5COR_6$, wherein said aryl or heteroaryl may be further substituted by one or more groups selected from the group consisting of alkyl, alkoxyl and halogen;

$R_5$ and $R_6$ are each independently selected from the group consisting of hydrogen and alkyl, wherein said alkyl may be further substituted by one or more groups selected from the group consisting of aryl, heteroaryl, haloaryl, hydroxyl, alkoxyl, aryloxyl, carboxylic acid and carboxylic ester;

$R_7$ is hydrogen or alkyl; and r is an integer from 1 to 6.

Representative compounds of this invention include, but are not limited to:

| Example No. | Structure | Name |
|---|---|---|
| 1 | 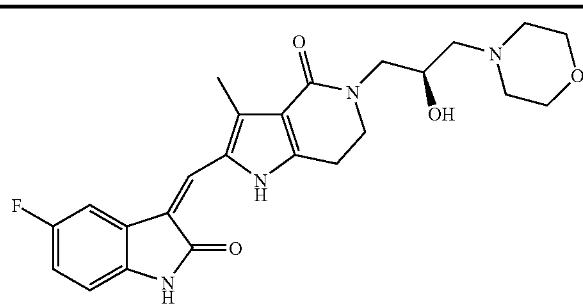 | (R,Z)-2-(5-Fluoro-2-oxo-1,2-dihydro-indol-3-ylidenemethyl)-5-(2-hydroxy-3 morpholin-4-yl-propyl)-3-methyl-1,5,6,7-tetrahydro-pyrrolo[3,2-c]pyridin-4-one |
| 2 | 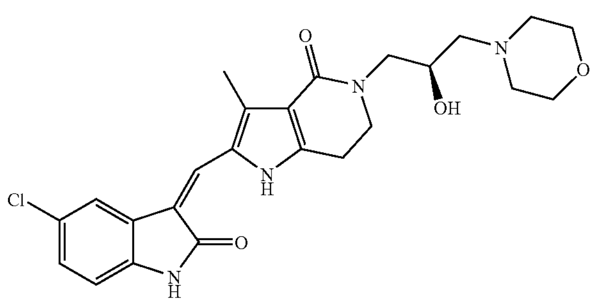 | (R,Z)-2-(5-Chloro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one |

-continued

| Example No. | Structure | Name |
|---|---|---|
| 3 | 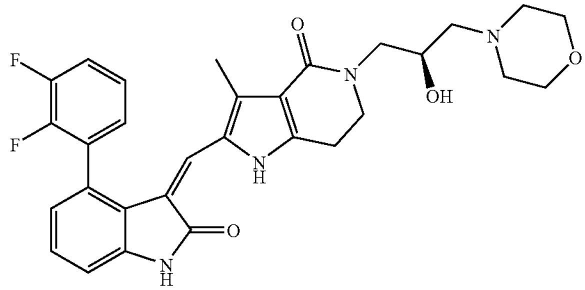 | 2-[(Z)-4-(2,3-Difluoro-phenyl)-2-oxo-1,2-dihydro-indol-3-ylidenemethyl]-5-[(R)-2-hydroxy-3-morpholin-4-yl-propyl]-3-methy-1,5,6,7-tetrahydro-pyrrolo[3,2-c]pyridin-4-one |
| 4 | 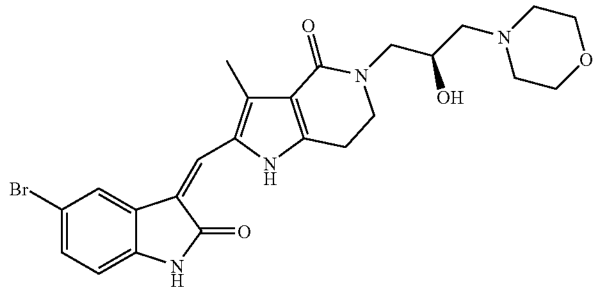 | (R,Z)-2-(5-Bromo-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one |
| 5 | 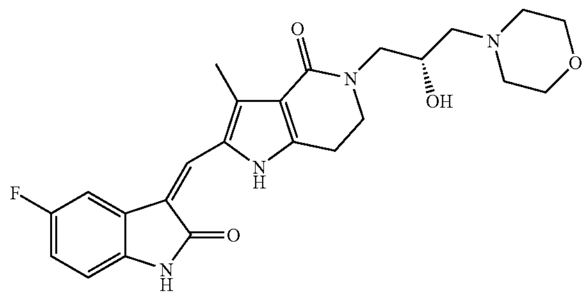 | (S,Z)-2-(5-Fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one |
| 6 | 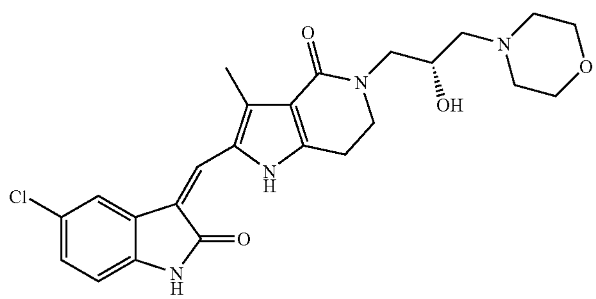 | (S,Z)-2-(5-Chloro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one |
| 7 | 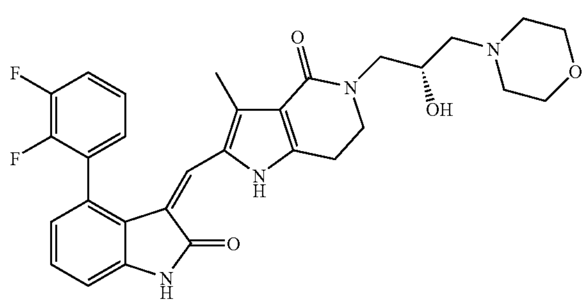 | 2-(Z)-[4-(2,3-Difluoro-phenyl)-2-oxo-1,2-dihydro-indol-3-ylidenemethyl]-5-[(S)-2-hydroxy-3-morpholin-4-yl-propyl]-3-methyl-1,5,6,7-tetrahydro-pyrrolo[3,2-c]pyridin-4-one |

-continued

| Example No. | Structure | Name |
|---|---|---|
| 8 | 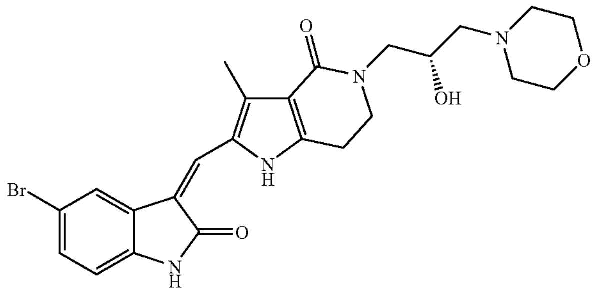 | (S,Z)-2-(5-bromo-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one |
| 9 | 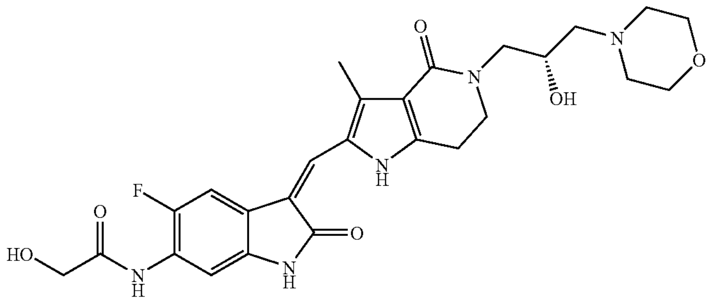 | (S,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-acetamide |
| 10 | 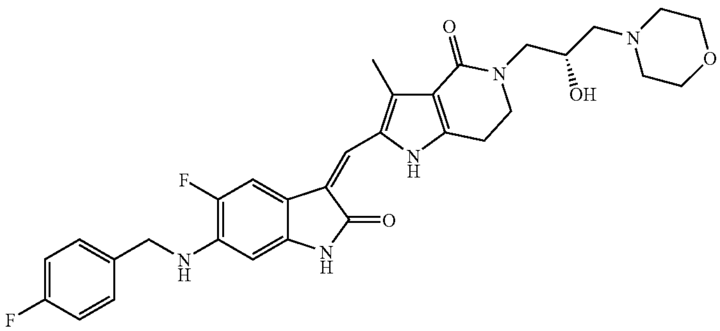 | (S,Z)-2-[5-Fluoro-6-(4-fluoro-benzylamino)-2-oxo-1,2-dihydro-indol-3-ylidenemethyl]-5-(2-hydroxy-3-morpholin-4-yl-propyl)-3-methyl-1,5,6,7-tetrahydro-pyrrolo[3,2-c]pyridin-4-one |
| 11 | 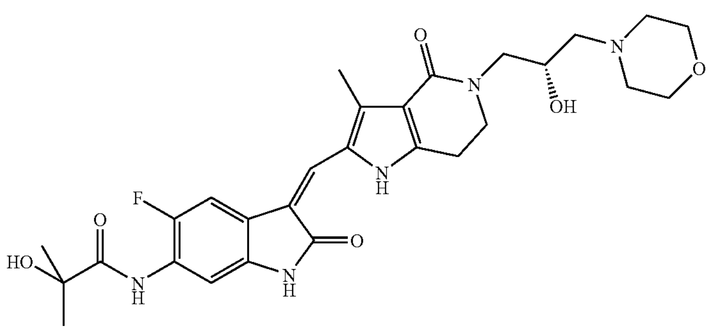 | (S,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide |
| 12 | 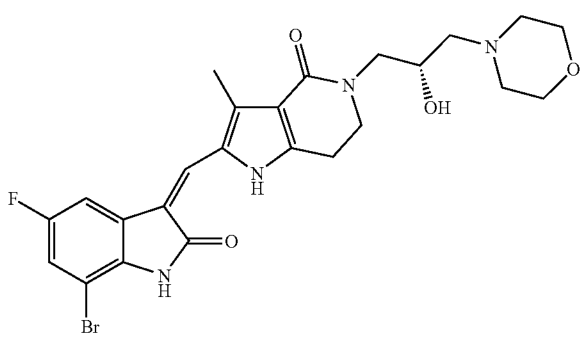 | (S,Z)-2-(7-Bromo-5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one |

| Example No. | Structure | Name |
|---|---|---|
| 13 | 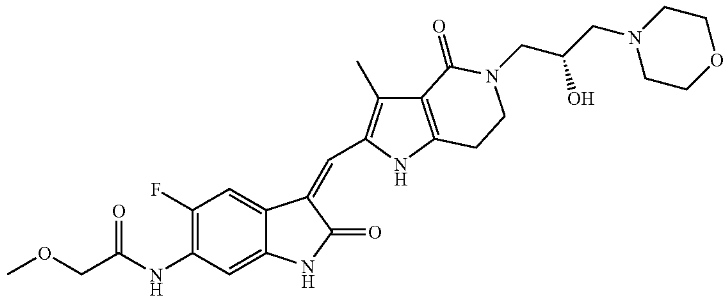 | (S,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide |
| 14 | 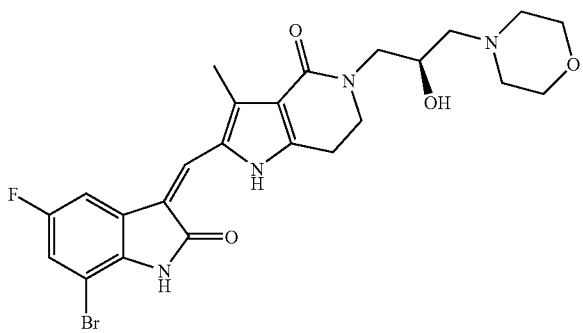 | (R,Z)-2-(7-Bromo-5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one |
| 15 | 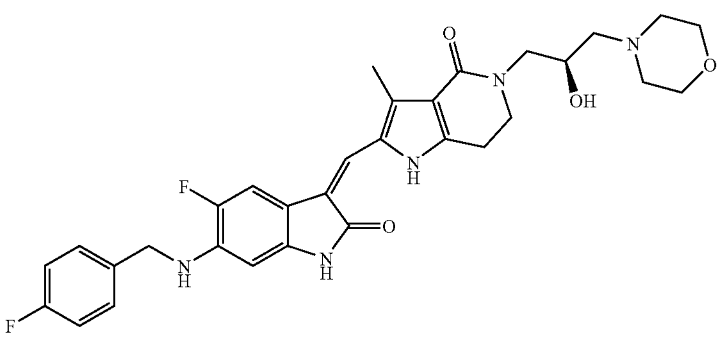 | (R,Z)-2-[5-Fluoro-6-(4-fluoro-benzylamino)-2-oxo-1,2-dihydro-indol-3-ylidenemethyl]-5-(2-hydroxy-3-morpholin-4-yl-propyl)-3-methyl-1,5,6,7-tetrahydro-pyrrolo[3,2-c]pyridin-4-one |
| 16 | 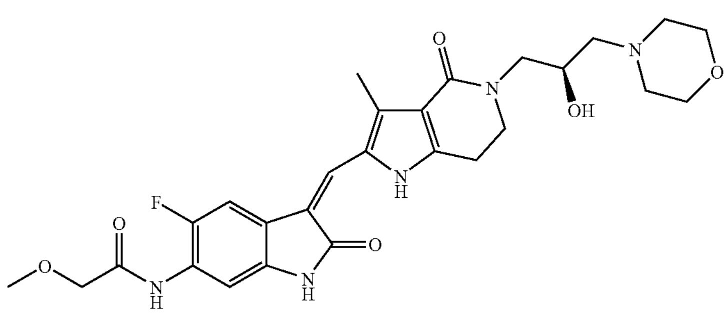 | (R,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide |

| Example No. | Structure | Name |
|---|---|---|
| 17 | 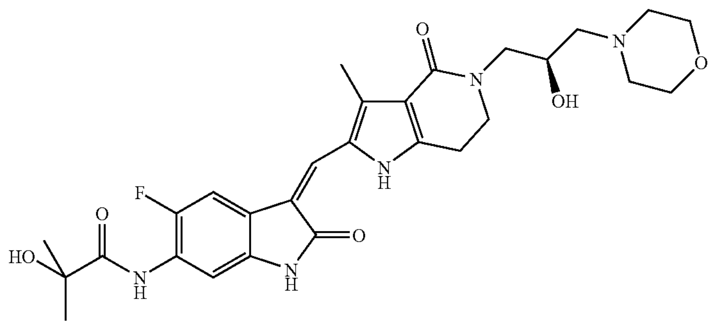 | (R,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide |
| 18 | 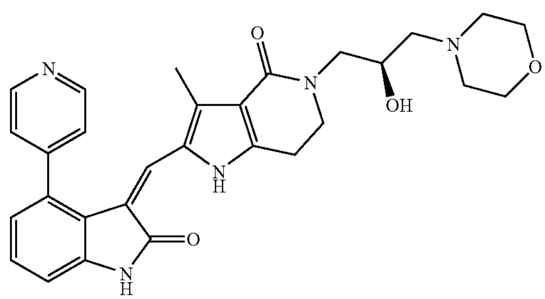 | (R,Z)-5-(2-Hydroxy-3-morpholin-4-yl-propyl)-3-methyl-2-(2-oxo-4-pyridin-4-yl-1,2-dihydro-indol-3-ylidenemethyl)-1,5,6,7-tetrahydro-pyrrolo[3,2-c]pyridin-4-one |
| 19 | 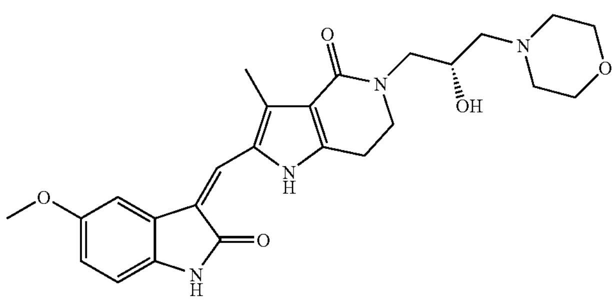 | (S,Z)-5-(2-Hydroxy-3-morpholin-4-yl-propyl)-2-(5-methoxy-2-oxo-1,2-dihydro-indol-3-ylidenemethyl)-3-methyl-1,5,6,7-tetrahydro-pyrrolo[3,2-c]pyridin-4-one |
| 20 | 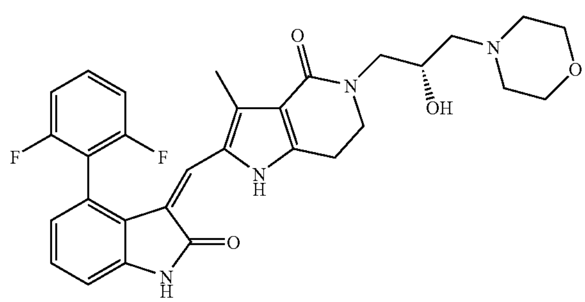 | (S,Z)-2-[4-(2,6-Difluoro-phenyl)-2-oxo-1,2-dihydro-indol-3-ylidenemethyl]-5-(2-hydroxy-3-morpholin-4-yl-propyl)-3-methyl-1,5,6,7-tetrahydro-pyrrolo[3,2-c]pyridin-4-one |
| 21 | 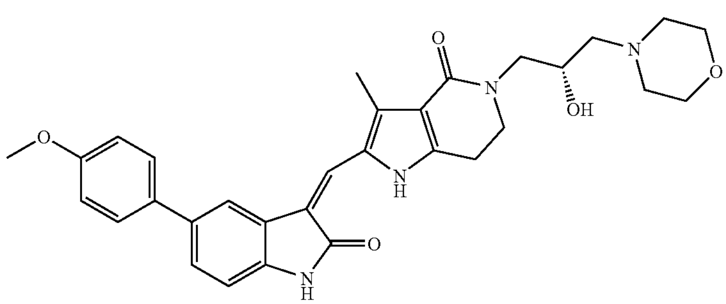 | (S,Z)-5-(2-Hydroxy-3-morpholin-4-yl-propyl)-2-[5-(4-methoxy-phenyl)-2-oxo-1,2-dihydro-indol-3-ylidenemethyl]-3-methyl-1,5,6,7-tetrahydro-pyrrolo[3,2-c]pyridin-4-one |

-continued

| Example No. | Structure | Name |
|---|---|---|
| 22 | 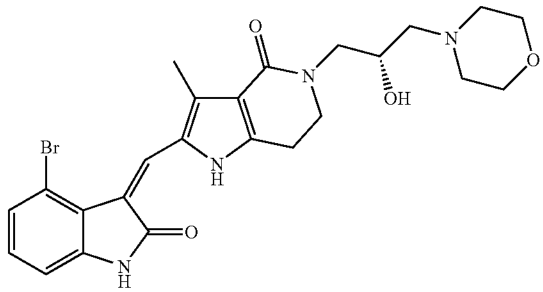 | (S,Z)-2-(4-Bromo-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one |
| 23 | 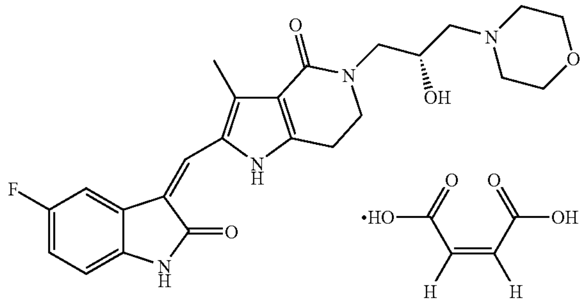 | (R,Z)-2-(5-Fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one maleate |
| 24 | | (R,Z)-2-(5-Fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one malate | or pharmaceutically acceptable salts thereof.

Wherein, the pharmaceutically acceptable salts according to present invention are the salts formed with the present compounds with the acids selected from malic acid, lactic acid, maleic acid, hydrochloric acid, methanesulfonic acid, sulfuric acid, phosphoric acid, citric acid, tartaric acid, acetic acid or trifluoroacetic acid, preferably, the acids are malic acid or maleic acid.

Another aspect of this invention is directed to a pharmaceutical composition comprising the compounds of pyrrolofused six-membered aza-heterocyclic hydroxyl morpholine derivatives having formula (I) or pharmaceutically acceptable salts thereof, carriers or excipients.

Another aspect of this invention is directed to a method of modulating the catalytic activity of a protein kinase, comprising contacting said protein kinase with the compounds of pyrrolofused six-membered aza-heterocyclic hydroxyl morpholine derivatives having formula (I) or pharmaceutically acceptable salts thereof, carriers or excipients. Said protein kinases are selected from receptor tyrosine kinases (RTKs), nonreceptor protein tyrosine kinases (CTKs) and serine/threonine protein kinases(STKs).

In another aspect, this invention is directed to the use of the compounds of pyrrolofused six-membered aza-heterocyclic hydroxyl morpholine derivatives having formula (I) in the preparation of medicament for the treatment of protein kinase related disorders. Wherein said the protein kinase related disorders are selected from the disorders related to EGFR, HER-2, HER-3, HER-4, PDGFR, VEGFR-2, c-Kit, c-Met, FGFR and Flt3.

Another aspect of this invention is the preparation process of pyrrolofused six-membered aza-heterocyclic hydroxyl morpholine derivatives having formula (I) or pharmaceutically acceptable salts thereof, wherein the preparation process comprises the following steps of:

heating the optically active compound of 1-amino-3-morpholin-4-yl-propan-2-ol (Ia) with 5-carboxymethyl-3-methyl-1H-pyrrole-2,4-dicarboxylic acid 2-tert-butyl ester 4-ethyl ester in acetonitrile in the presence of 1-hydroxybenzotriazol and N-ethyl-N'-(dimethylaminopropyl)-carbodiimide to obtain chiral pyrrole amide dicarboxylic acid diester (Ib) under a nitrogen atmosphere;

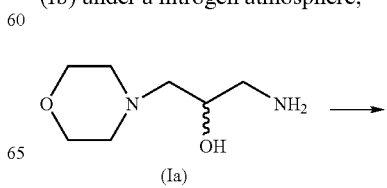

(Ia)

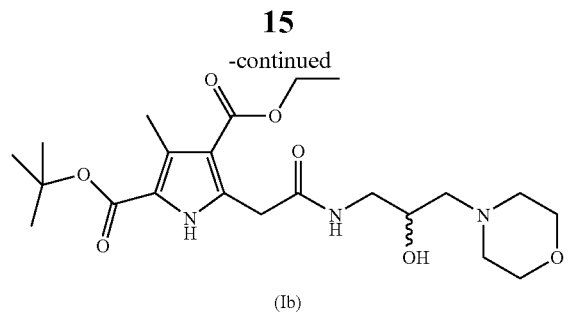

(Ib)

heating chiral pyrrole amide dicarboxylic acid diester (Ib) with hydrochloric acid to reflux in ethanol to obtain optically active pyrrole amide ethyl ester (Ic) under an argon atmosphere;

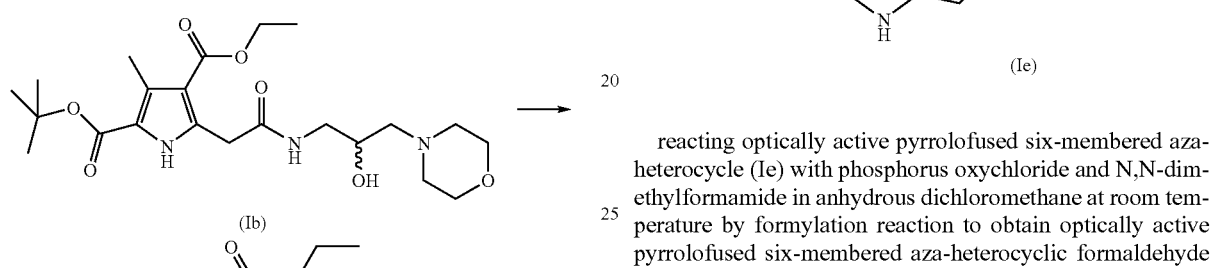

further, heating optically active pyrrole amide ethyl ester (Ic) with borane to reflux in anhydrous tetrahydrofuran by selective reduction to obtain chirally substituted pyrrole ethyl ester (Id);

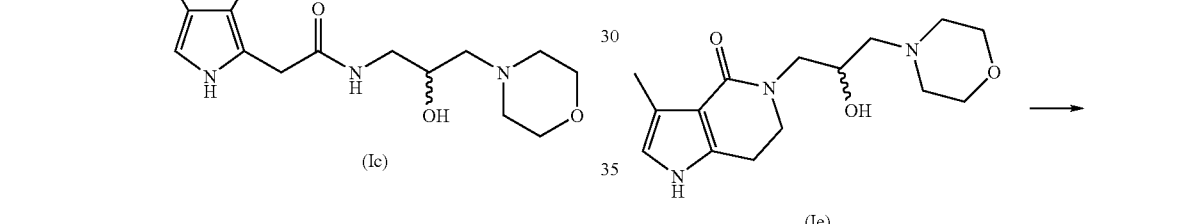

then, heating chirally substituted pyrrole ethyl ester (Id) with lithium hydroxide monohydrate to reflux in glycol to obtain the cyclized product of optically active pyrrolofused six-membered aza-heterocycle (Ie) under an argon atmosphere;

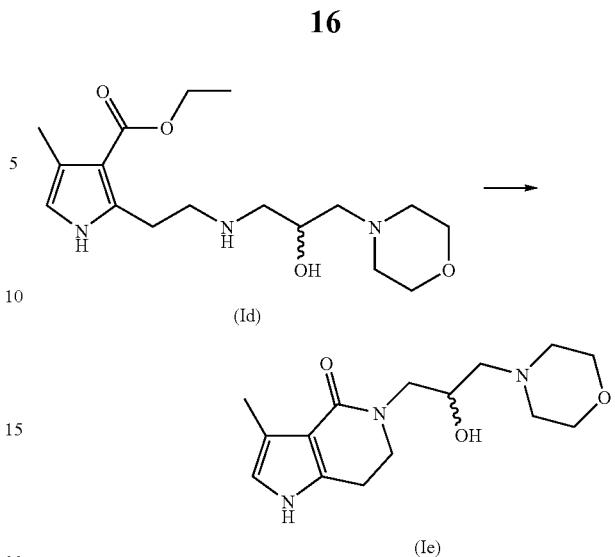

reacting optically active pyrrolofused six-membered aza-heterocycle (Ie) with phosphorus oxychloride and N,N-dimethylformamide in anhydrous dichloromethane at room temperature by formylation reaction to obtain optically active pyrrolofused six-membered aza-heterocyclic formaldehyde (If);

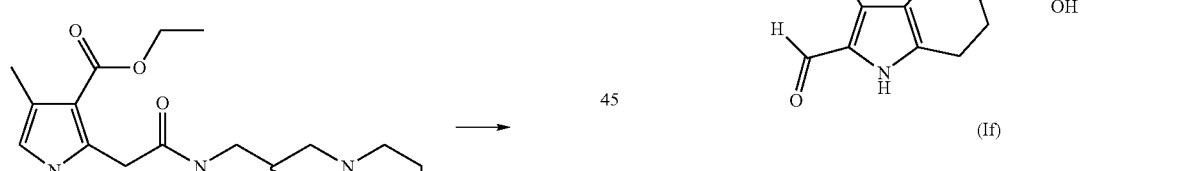

finally, heating optically active pyrrolofused six-membered aza-heterocyclic formaldehyde (If) with different indolinones in the presence of a base such as triethylamine or piperidine for 2~12 hours to obtain the target product of chiral pyrrolofused six-membered aza-heterocyclic hydroxyl morpholine derivatives of formula (I);

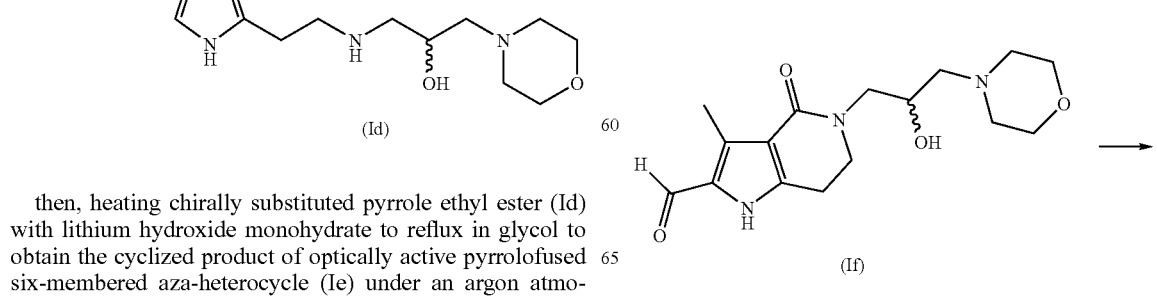

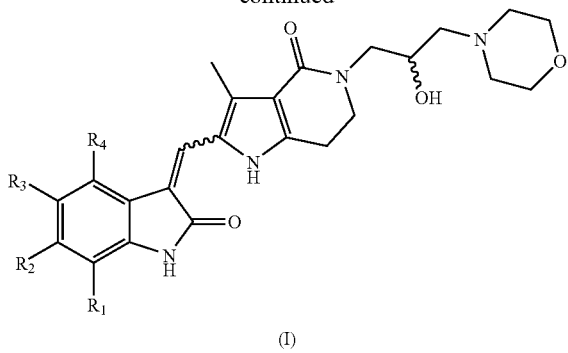

(I)

wherein: $R_1$, $R_2$, $R_3$, $R_4$ are as defined above.

DETAILED DESCRIPTION OF THE INVENTION

Unless otherwise stated, the following terms used in the description and claims have the meanings discussed below.

"Alkyl" refers to a saturated aliphatic hydrocarbon group including straight chain and branched chain groups of 1 to 20 carbon atoms. Preferably, an alkyl group is a middle size alkyl having 1 to 10 carbon atoms, e.g., methyl, ethyl, propyl, 2-propyl, n-butyl, iso-butyl, tert-butyl, pentyl, and the like. More preferably, it is a lower alkyl having 1 to 4 carbon atoms, e.g., methyl, ethyl, propyl, 2-propyl, n-butyl, iso-butyl, or tert-butyl, and the like. The alkyl group may be substituted or unsubstituted. When substituted, the substituent group(s) may be seleted from the group consisting of halo, hydroxyl, alkoxyl, aryl, heteroaryl, haloaryl, aryloxyl, carboxylic acid, carboxylic ester, —$OR_5$, —$O[CH_2CH_2O]_rR_7$, —$NR_5R_6$, —$COR_5$ and —$NR_5COR_6$.

"Aryl" refers to groups having at least one aromatic ring, i.e., having a conjugated pi-electron system, including all-carbon cyclic aryl, heteroaryl and biaryl group. Said aryl group may be substituted or unsubstituted. When substituted, the substituent group(s) may be seleted from the group consisting of halo, alkoxyl, alkyl, hydroxyl, aryloxyl, carboxylic acid, carboxylic ester, —$OR_5$, —$O[CH_2CH_2O]_rR_7$, —$NR_5R_6$, —$COR_5$ and —$NR_5COR_6$.

"Heteroaryl" refers to an aryl having one to three ring heteroatoms selected from the group consisting of O, S, and N as ring atoms, the remaining ring atoms being C. Said ring is 5 or 6 membered ring. The examples of heteroaryl groups include furyl, thienyl, pyridyl, pyrrolyl, N-alkyl pyrrolyl, pyrimidinyl, pyrazinyl, imidazolyl, and the like. The heteroaryl group may be substituted or unsubstituted. When substituted, the substituent group(s) may be seleted from the group consisting of halo, alkoxyl, alkyl, hydroxyl, aryloxyl, carboxylic acid, carboxylic ester, —$OR_5$, —$O[CH_2CH_2O]_rR_7$, —$NR_5R_6$, —$COR_5$ and —$NR_5COR_6$.

"Hydroxyl" refers to an —OH group.

"Alkoxyl" refers to both an —O-(alkyl) and an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like. The alkoxyl group may be substituted or unsubstituted. When substituted, the substituent group(s) may be seleted from the group consisting of halo, hydroxyl, alkoxyl, aryl, heteroaryl, haloaryl, aryloxyl, carboxylic acid, carboxylic ester, —$OR_5$, —$O[CH_2CH_2O]_rR_7$, —$NR_5R_6$, —$COR_5$ and —$NR_5COR_6$.

"Aryloxyl" refers to both an —O-aryl and an —O-heteroaryl group, wherein the aryl and heteroaryl are as defined above. Representative examples include, but are not limited to, phenoxy, pyridinyloxy, furanyloxy, thienyloxy, pyrimidinyloxy, pyrazinyloxy, and the like, and derivatives thereof. The aryloxyl group may be substituted or unsubstituted. When substituted, the substituent group(s) may be seleted from the group consisting of halo, alkoxyl, alkyl, hydroxyl, aryloxyl, carboxylic acid, carboxylic ester, —$OR_5$, —$O[CH_2CH_2O]_rR_7$, —$NR_5R_6$, —$COR_5$ and —$NR_5COR_6$.

"Halo" refers to fluoro, chloro, bromo, or iodo, preferably fluoro or chloro.

"Haloalkoxy" refers to an —O-(haloalkyl). Representative examples include, but are not limited to, trifluoromethoxy, tribromoethoxy, and the like.

"Carboxylic acid" refers to a (alkyl)C(=O)OH.

"Carboxylate" refers to a (alkyl)C(=O)O(alkyl).

"Optional" or "optionally" means that the subsequently described event or circumstance may or may not occur, and that the description includes instances where the event or circumstance may or may not occur. For example, "heterocycle group optionally substituted with an alkyl group" means that the alkyl may or may not be present, and the description includes situations where the heterocycle group is substituted with an alkyl group and situations where the heterocyclo group is not substituted with the alkyl group.

A "pharmaceutical composition" refers to a mixture of one or more of the compounds described herein or physiologically/pharmaceutically acceptable salts or prodrugs thereof, with other chemical components, such as physiologically/pharmaceutically acceptable excipients. The purpose of a pharmaceutical composition is to facilitate administration of a compound to an organism.

Methods of Preparation

In order to complete the objective of the present invention, the invention applies the following technical solution:

A preparation process of compounds of pyrrolofused six-membered aza-heterocyclic hydroxyl morpholine derivatives of formula (I) or pharmaceutically acceptable salts thereof, comprising the following steps of:

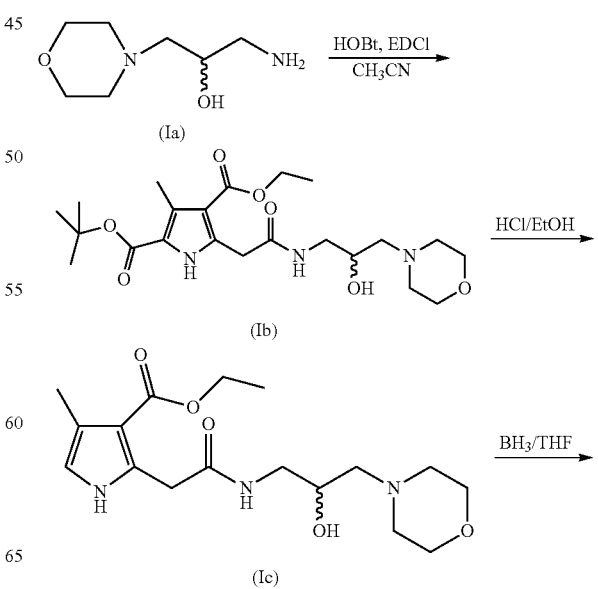

-continued

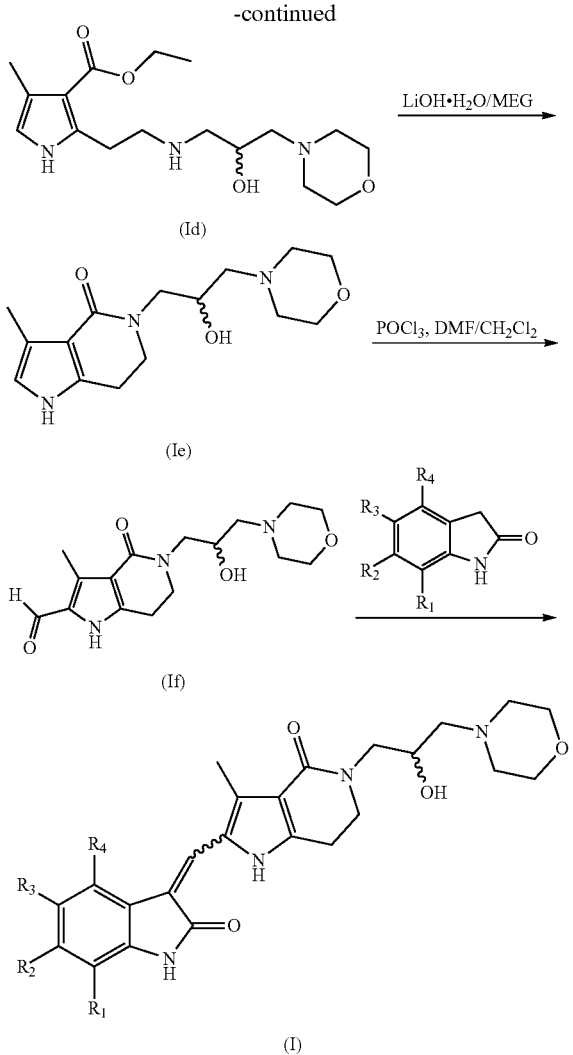

The optically active compound of 1-amino-3-morpholin-4-yl-propan-2-ol (Ia) (prepared according to the patent US20040209937) as the start material, heating optically active 1-amino-3-morpholin-4-yl-propan-2-ol (Ia) with 5-carboxymethyl-3-methyl-1H-pyrrole-2,4-dicarboxylic acid 2-tert-butyl ester 4-ethyl ester to reflux in the presence of 1-hydroxybenzotriazol and N-ethyl-N'-(dimethylaminopropyl)-carbodiimide in acetonitrile to obtain chiral pyrrole amide dicarboxylic acid diester (Ib) under a nitrogen atmosphere; heating chiral pyrrole amide dicarboxylic acid diester (Ib) with hydrochloric acid to reflux in ethanol to obtain optically active pyrrole amide ethyl ester (Ic) under an argon atmosphere; further, heating optically active pyrrole amide ethyl ester (Ic) with borane to reflux in anhydrous tetrahydrofuran by selective reduction to obtain chirally substituted pyrrole ethyl ester (Id); then, heating chirally substituted pyrrole ethyl ester (Id) with lithium hydroxide monohydrate to reflux in glycol to obtain the cyclized product of optically active pyrrolofused six-membered aza-heterocycle (Ie) under an argon atmosphere; reacting optically active pyrrolofused six-membered aza-heterocycle (Ie) with phosphorus oxychloride and N,N-dimethylformamide in anhydrous dichloromethane at room temperature by formylation reaction to obtain optically active pyrrolofused six-membered aza-heterocyclic formaldehyde (If); finally, heating optically active pyrrolofused six-membered aza-heterocyclic formaldehyde (If) with different indolinones in the presence of a base such as triethylamine or piperidine for 2~12 hours to obtain the target product of chiral pyrrolofused six-membered heterocyclic hydroxyl morpholine derivatives of formula (I). Wherein, the key technique is selective reduction of the substrate (Ic) by borane and the catalyzed cyclization of the substrate (Id) by the base catalyst lithium hydroxide monohydrate. Especially the latter, there are no related references about the approach to construct such pyrrolofused six-membered lactam structure.

This invention also relates to a pharmaceutical composition comprising a compound of formula (I) or salt thereof in an effective therapeutic dose, as well as pharmaceutically acceptable carriers.

This invention further relates to the use of the compounds of the invention of formula (I) or salts thereof in the preparation of a medicament as protein kinase inhibitor.

Preferred Embodiments

The following examples serve to illustrate the invention, but the examples should not be considered as limiting the scope of the invention.

The compound's structure was identified by nuclear magnetic resonance (NMR) or mass spectrometry (MS). NMR chemical shifts (δ) were given in parts per million (ppm). NMR was determined by a Bruker AVANCE-400 machine. The solvent were deuterated-chloroform ($CDCl_3$) and deuterated-dimethyl sulfoxide (DMSO-d6) with tetramethylsilane (TMS) as internal standard. Chemical shifts were given in parts per million (ppm).

MS was determined by a FINNIGAN LCQAd (ESI) mass spectrometer.

Thin-layer silica gel was Yantai Huanghai HSGF254 or Qingdao GF254 silica gel plate.

Column chromatography generally used Yantai Huanghai 200-300 mesh silica gel as carrier.

DMSO-$D_6$: deutorated dimethyl sulfoxide.

$CDCl_3$: deutorated chloroform.

PREPARATION EXAMPLES

Example 1

(R,Z)-2-(5-Fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one

1

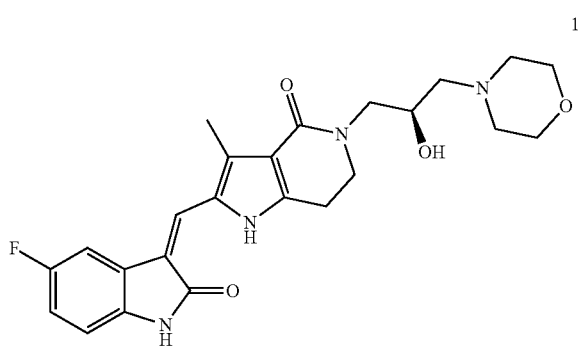

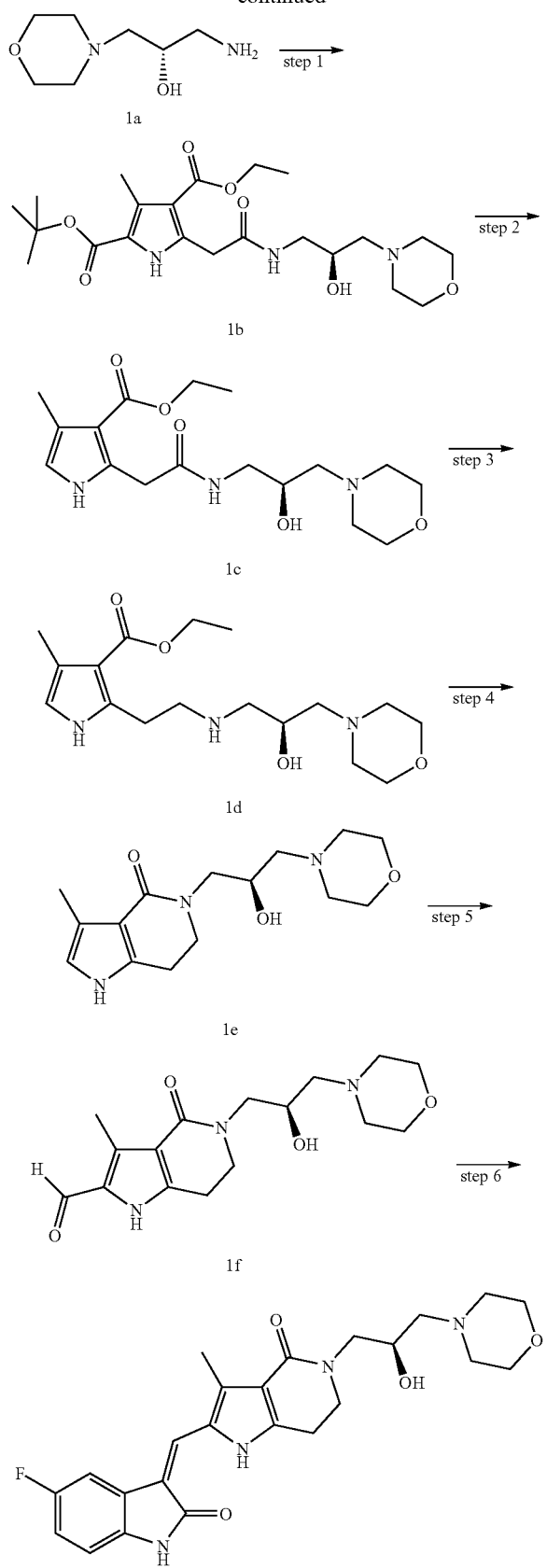

Step 1

5-[(2-Hydroxy-3-morpholin-4-yl-propylcarbamoyl)-methyl]-3-methyl-1H-pyrrole-2,4-dicarboxylic acid (S)-2-tert-butyl ester 4-ethyl ester (S)-1-Amino-3-morpholin-4-yl-propan-2-ol 1a (15.125 g, 94.5 mmol), 5-carboxymethyl-3-methyl-1H-pyrrole-2,4-dicarboxylic acid 2-tert-butyl ester 4-ethyl ester (32.34 g, 104 mmol), 1-hydroxybenzotriazol (25.5 g, 189.06 mmol) and N-ethyl-N'-(dimethylaminopropyl)-carbodiimide (36.2 g, 189.06 mmol) were dissolved in 450 mL of acetonitrile under stirring at room temperature, and the reaction mixture was stirred at 50° C. in an oil bath for 3 hours. The reaction was completed until Thin Layer Chromatography (TLC) showed the disappearance of starting materials, and the solvent was evaporated under reduced pressure, and 150 mL of saturated brine was then added to the residue. The mixture was extracted with the solvent mixture of ethyl acetate and tetrahydrofuran (V:V=4:1, 200 mL ×5). The combined organic extracts were washed with saturated brine (100 mL), dried over anhydrous magnesium sulfate and filtered to remove the drying agent. The filtrate was concentrated under reduced pressure to give an oil (75 g). The oil was purified by silica gel column chromatography to give the title compound 5-[(2-hydroxy-3-morpholin-4-yl-propylcarbamoyl)-methyl]-3-methyl-1H-pyrrole-2,4-dicarboxylic acid (S)-2-tert-butyl ester 4-ethyl ester 1b (30 g, yield 70%) as a light brown solid.

MS m/z (ESI): 454.4[M+1]

Step 2

(S)-2-[(2-Hydroxy-3-morpholin-4-yl-propylcarbamoyl)-methyl]-4-methyl-1H-pyrrole-3-carboxylic acid ethyl ester 5-[(2-Hydroxy-3-morpholin-4-yl-propylcarbamoyl)-methyl]-3-methyl-1H-pyrrole-2,4-dicarboxylic acid (S)-2-tert-butyl ester 4-ethyl ester 1b (25.7 g, 56.7 mmol) was dissolved in 70 mL of anhydrous ethanol under stirring under an argon atmosphere, and 71 mL of hydrochloric acid (12 N) was then added dropwise to the solution in an ice-water bath. Upon completion of the addition, the ice-water bath was removed. The reaction system was stirred at 60° C. in an oil bath for 1.5 hours. The reaction was completed until TLC showed the disappearance of starting materials, and the reaction system was adjusted to pH about 7 with 10N sodium hydroxide solution in a dry ice-acetone bath and lots of precipitates were formed. The mixture was filtered and the filter cake was washed with ethanol. The filtrate was concentrated under reduced pressure to remove the solvent, and the residue was adjusted to pH about 10 with 10N sodium hydroxide solution. The mixture was extracted with dichloromethane (150 mL ×3). The combined organic extracts were washed with saturated brine (100 mL), dried over anhydrous magnesium sulfate, filtered to remove the drying agent and concentrated under reduced pressure to give the title compound (S)-2-[(2-hydroxy-3-morpholin-4-yl-propylcarbamoyl)-methyl]-4-methyl-1H-pyrrole-3-carboxylic acid ethyl ester 1c (16.9 g, yield 84%) as a dark green oil.

MS m/z (ESI): 354.3[M+1]

Step 3

(S)-2-[2-(2-Hydroxy-3-morpholin-4-yl-propylamino)-ethyl]-4-methyl-1H-pyrrole-3-carboxylic acid ethyl ester (S)-2-[(2-Hydroxy-3-morpholin-4-yl-propylcarbamoyl)-methyl]-4-methyl-1H-pyrrole-3-carboxylic acid ethyl ester 1c (16.9 g, 47.9 mmol) was dissolved in 143.6 mL of anhydrous tetrahydrofuran under an argon atmosphere, and borane-tertrahydrofuran complex in tetrahydrofuran (143.6 mL, 1 mol/L, 143.6 mmol) was then added to the solution in an ice-water bath. Upon completion of the addition, the ice-water bath was removed. The reaction system was allowed to warm up to room temperature and refluxed at 95° C. in an oil bath for 1 hour and. The reaction was completed until TLC showed the disappearance of starting materials. The solvent was evaporated under reduced pressure, and 150 mL of hydrochloric acid (2N) was then added to the residue. The mixture was stirred for 0.5 hour, and 50 mL of iced water was then added. The mixture was adjusted to pH about 10 with 10N sodium hydroxide solution and extracted with ethyl acetate (200 mL ×2). The combined organic extracts were washed with saturated brine (100 mL), dried over anhydrous magnesium sulfate, filtered to remove the drying agent and concentrated under reduced pressure to give the title compound (S)-2-[2-(2-hydroxy-3-morpholin-4-yl-propylamino)-ethyl]-4-methyl-1H-pyrrole-3-carboxylic acid ethyl ester 1d (15.6 g, yield 96%) as a brown oil.

MS m/z (ESI): 340.3[M+1]

Step 4

(R)-5-(2-Hydroxy-3-morpholin-4-yl-propyl)-3-methyl-1,5,6,7-tetrahydro-pyrrolo[3,2-c]pyridin-4-one (S)-2-[2-(2-Hydroxy-3-morpholin-4-yl-propylamino)-ethyl]-4-methyl-1H-pyrrole-3-carboxylic acid ethyl ester 1d (16.2 g, 47.9 mmol) and lithium hydroxide monohydrate (8 g, 190.6 mmol) were dissolved in 50 mL of glycol under stirring under an argon atmosphere. The reaction system was stirred at 135° C. in an oil bath for 50 minutes. The reaction was completed until TLC showed the disappearance of starting materials. The solvent was evaporated under reduced pressure, and 150 mL of saturated brine was then added to the residue. The mixture was extracted with dichloromethane (150 mL ×5). The combined organic extracts were washed with saturated brine (150 mL), dried over anhydrous magnesium sulfate, filtered to remove the drying agent and concentrated under reduced pressure to give the oil (12.3 g). The oil was purified by silica gel column chromatography to give the title compound (R)-5-(2-hydroxy-3-morpholin-4-yl-propyl)-3-methyl-1,5,6,7-tetrahydro-pyrrolo[3,2-c]pyridin-4-one 1e (7.9 g, yield 60.6%) as a white solid.

MS m/z (ESI): 294.2[M+1]

Step 5

(R)-5-(2-Hydroxy-3-morpholin-4-yl-propyl)-3-methyl-4-oxo-4,5,6,7-tetrahydro-1H-pyrrolo[3,2-c]pyridine-2-carbaldehyde Phosphorus oxychloride (674 µL, 4.04 mmol) and N,N-dimethylformamide (963 µL, 12.32 mmol) were dissolved in 21.18 mL of dichloromethane under stirring at room temperature, and the reaction solution was stirred for 15 minutes while maintaining the temperature at −10° C. in an ice-water bath. (R)-5-(2-hydroxy-3-morpholin-4-yl-propyl)-3-methyl-1,5,6,7-tetrahydro-pyrrolo[3,2-c]pyridin-4-one 1e (790 mg, 2.7 mmol) was dissolved in 10 mL of dichloromethane under stirring, and the solution was then added dropwise to the above reaction system. Upon completion of the addition, the ice-water bath was removed, and the reaction system was allowed to warm up to room temperature and stirred for another 2 hours. The reaction was completed until TLC showed the disappearance of starting materials, and the reaction system was quenched with iced water and stirred for 15 minutes. The mixture was adjusted to pH about 12 with 10N sodium hydroxide solution and extracted with the solvent mixture of dichloromethane and methanol (V:V=20:1, 100 mL ×8). The combined organic extracts were washed with saturated brine (150 mL), dried over anhydrous magnesium sulfate, filtered to remove the drying agent and concentrated under reduced pressure to give the crude product (800 mg). The crude product was purified by silica gel column chromatography to give the title compound (R)-5-(2-hydroxy-3-morpholin-4-yl-propyl)-3-methyl-4-oxo-4,5,6,7tetrahydro-1H-pyrrolo[3,2-c]pyridine-2-carbaldehyde 1f (650 mg, yield 75%) as a white solid.

MS m/z (ESI): 322.6[M+1]

Step 6

(R,Z)-2-(5-Fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one (R)-5-(2-Hydroxy-3-morpholin-4-yl-propyl)-3-methyl-4-oxo-4,5,6,7-tetrahydro-1H-pyrrolo[3,2-c]pyridine-2-carbaldehyde 1f (200 g, 0.623 mmol), 5-fluoro-1,3-dihydro-indol-2-one (84.67 mg, 0.56 mmol) and piperidine (30.8 µL, 0.31 mmol) were dissolved in 1.09 mL of ethanol under stirring at room temperature. The reaction system was stirred at 80° C. in an oil bath in dark for 2 hours.The reaction was completed until TLC showed the disappearance of starting materials, and the oil bath was removed. The reaction system was allowed to cool down to room temperature to precipitate solids. The resulting solids were filtered to give the title compound (R,Z)-2-(5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 1 (256 mg, 90%) as a yellow solid.

MS m/z (ESI): 455.2[M+1]

[1] HNMR (400 MHz, DMSO-d6): 13.674 (s, 1H, pyrrole-NH), 10.945(s, 1H, indole-NH), 7.771~7.800(m, 1H, —ArH), 7.762(s, 1H, —CH=C), 6.927~6.978(dd, 1H, —ArH), 6.842~6.874(d, 1H, —ArH), 4.707~4.719(d, 1H, —OH), 3.900~3.915(m, 1H, —CHO), 3.704~3.748(dd, 2H, amide N six-membered ring intra-CH$_2$—), 3.616~3.695(dd, 1H, amide N six-membered ring outer-CH$_2$—), 3.563~3.585 (t; 4H, morpholine 2×—CH$_2$O), 3.105~3.158(dd, 1H, amide N six-membered ring outer-CH$_2$—), 3.433(t, 2H, six-membered ring linked to pyrrole-CH$_2$—), 2.545(s, 3H, pyrrole-CH$_3$), 2.420~2.431(m, 2H, —CH$_2$N, morpholine-CH$_2$N), 2.420~2.431(m, 2H, —CH$_2$N, morpholine outer-CH$_2$N), 2.304~2.330(t, 2H, morpholine intra —CH$_2$N)

Example 2

(R,Z)-2-(5-Chloro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one

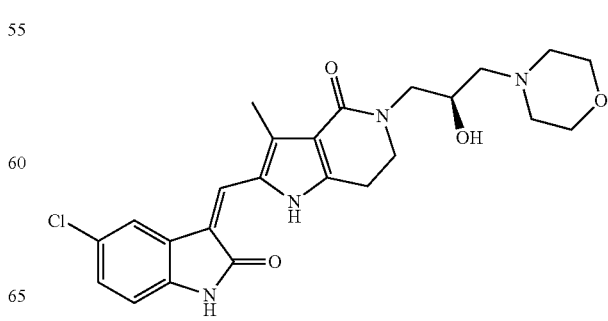

The title compound was prepared under the same conditions as described in step 6 of Example 1 with (R)-5-(2-hydroxy-3-morpholin-4-yl-propyl)-3-methyl-4-oxo-4,5,6,7-tetrahydro-1H-pyrrolo[3,2-c]pyridine-2-carbaldehyde 1f obtained from step 5 of Example 1 and 5-chloro-1,3-dihydro-indol-2-one as starting materials to give (R,Z)-2-(5-chloro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 2 (42 mg, yield 64%) as a yellow solid.

MS m/z (ESI): 471.2[M+1]

$^1$HNMR (400MHz, DMSO-d6): 13.727(s, 1H, pyrrole-NH), 11.039(s, 1H, indole-NH), 8.003(m, 1H, —ArH), 7.814 (s, 1H, —CH=C), 7.166~7.141(dd, 1H, —ArH), 6.890~6.869(d, 1H, —ArH), 4.713~4.700(d, 1H, —OH), 3.907~3.892(m, 1H, —CHO), 3.626~3.567(t, 4H, morpholine 2×—CH$_2$O), 3.152~3.099(dd, 1H, amide N six-membered ring outer-CH$_2$—), 3.027~2.994(t, 2H, six-membered ring linked to pyrrole-CH$_2$—), 2.547 (s, 3H, pyrrole-CH$_3$), 2.328~2.290(t, 2H, morpholine intra —CH$_2$N)

Example 3

2-[(Z)-4-(2,3-Difluoro-phenyl)-2-oxo-1,2-dihydro-indol-3-ylidenemethyl]-5-[(R)-2-hydroxy-3-morpholin-4-yl-propyl]-3-methyl-1,5,6,7-tetrahydro-pyrrolo[3,2-c]pyridin-4-one

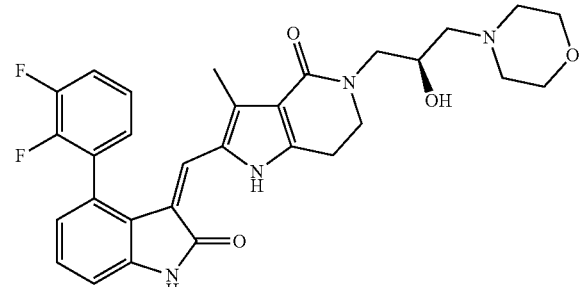

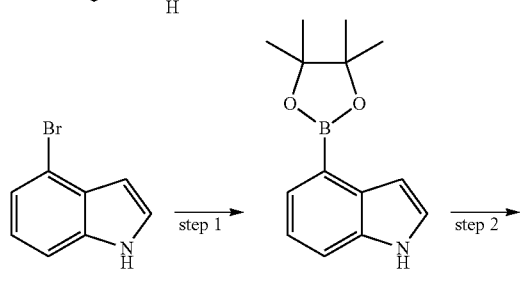

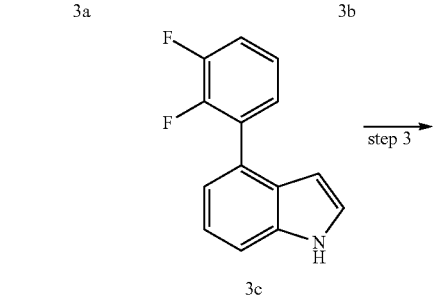

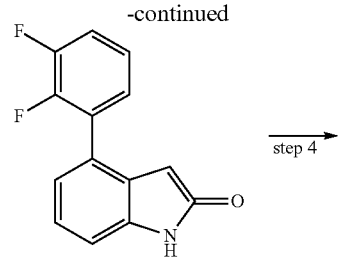

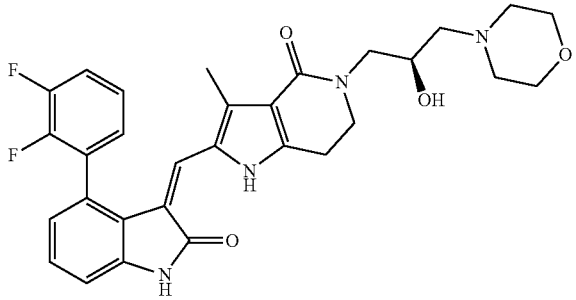

Step 1

4-(4,4,5,5-Tetramethyl-[1,3,2]dioxaborolan-2-yl)-1H-indole

4-Bromo-1H-indole 3a (29.4 g, 150 mmol) was dissolved in 600 mL of dimethyl sulfoxide under stirring under an argon atmosphere, and bis(pinacolato)diboron (41.9 g, 165 mmol), potassium acetate (44.1 g, 450 mmol) and [1,1'-bis(diphenylphosphino)ferrocene] dichloropalladium (3.6 g, 4.8 mmol) were then added to the solution. Upon completion of the addition, the reaction mixture was stirred at 80° C. in an oil bath for 22 hours. The reaction was completed until TLC showed the disappearance of starting materials, and 2 L of water was added to the reaction mixture. The mixture was extracted with ethyl acetate (2 L ×3). The combined organic extracts were washed with saturated brine (2 L ×5), dried over anhydrous sodium sulfate, filtered to remove the drying agent and concentrated under reduced pressure. The residue was purified by silica gel column chromatography and recrystallized to give the title compound 4-(4,4,5,5-tetramethyl-[1,3,2]dioxaborolan-2-yl)-1H-indole 3b (20 g, yield 60%) as a white solid.

MS m/z (ESI): 243.9[M+1]

Step 2

4-(2,3-difluoro-phenyl)-1H-indole 4-(4,4,5,5-Tetramethyl-[1,3,2]dioxaborolan-2-yl)-1H-indole 3b (1.22 g, 5 mmol) was dissolved in 20 mL of tetrahydrofuran under stirring under an argon atmosphere, and 1-bromo-2,3-difluoro-benzene (0.97 g, 5 mmol), tetrakis(triphenylphosphine) palladium (0.17 g, 0.15 mmol) and 7 mL of sodium hydroxide solution (2M) were then added to the solution. Upon completion of the addition, the reaction system was stirred at 75° C. in an oil bath overnight. The reaction was completed until TLC showed the disappearance of starting materials. The reaction mixture was naturally cooled down to room temperature and extracted with ethyl acetate (20 mL ×3). The combined organic extracts were washed with saturated brine (10 mL), dried over anhydrous sodium sulfate, filtered to remove the drying agent and concentrated under reduced pressure. The resulting solid was purified by silica gel column chromatography to give the title compound 4-(2,3-difluoro-phenyl)-1H-indole 3c (800 mg, yield 70%) as a white solid.

MS m/z (ESI): 228.4[M−1]

Step 3

4-(2,3-Difluoro-phenyl)-1,3-dihydro-indol-2-one 4-(2,3-Difluoro-phenyl)-1H-indole 3c (744 mg, 3.25 mmol) was dissolved in 12 mL of ethanol under stirring at room temperature, and 21 mL of tert-butanol, 6.4 mL of glacial acetic acid and pyridinium tribromide (3.12 g, 9.7 mmol) were then added successively to the solution. Upon completion of the addition, the reaction mixture was stirred for 3 hours, and 16 mL of glacial acetic acid and zinc dust (1.1 g, 16.25 mmol) were then added to the mixture. The reaction mixture was stirred for another 1 hour, filtered to remove the residue and concentrated under reduced pressure. The residue was added with 30 mL of ethyl acetate, washed successively with 10 mL of water, 10 mL of saturated sodium bicarbonate solution and 10 mL of saturated brine, dried over anhydrous sodium sulfate and filtered to remove the drying agent. The filtrate was concentrated under reduced pressure to give the title compound 4-(2,3-difluoro-phenyl)-1,3-dihydro-indol-2-one 3d (780 mg, yield 97%) as a white solid.

MS m/z (ESI): 246.6[M+1]

Step 4

2-[(Z)-4-(2,3-Difluoro-phenyl)-2-oxo-1,2-dihydro-indol-3-ylidenemethyl]-5-[(R)-2-hydroxy-3-morpholin-4-yl-propyl]-3-methyl-1,5,6,7-tetrahydro-pyrrolo[3,2-c]pyridin-4-one (R)-5-(2-Hydroxy-3-morpholin-4-yl-propyl)-3-methyl-4-oxo-4,5,6,7-tetrahydro-1H-pyrrolo[3,2-c]pyridine-2-carbaldehyde 1f (50 mg, 0.156 mmol), 4-(2,3-difluoro-phenyl)-1,3-dihydro-indol-2-one 3d (34.3 mg, 0.14 mmol) and piperidine (7.7 µL, 0.078 mmol) were dissolved in 0.3 mL of ethanol under stirring at room temperature. The reaction system was stirred at 80° C. in an oil bath in dark for 2 hours. The reaction was completed until TLC showed the disappearance of starting materials, and the oil bath was removed. The reaction system was naturally cooled down to room temperature to precipitate solids. The resulting solids were filtered to give the title compound 2-[(Z)-4-(2,3-difluoro-phenyl)-2-oxo-1,2-dihydro-indol-3-ylidenemethyl]-5-[(R)-2-hydroxy-3-morpholin-4-yl-propyl]-3-methyl-1,5,6,7-tetrahydro-pyrrolo[3,2-c]pyridin-4-one 3 (56 mg, yield 73%) as a yellow solid.

MS m/z (ESI): 549.3[M+1]

$^1$HNMR (400 MHz, DMSO-d6): 13.583(s, 1H, pyrrole-NH), 11.164 (s, 1H, indole-NH), 7.647~7.604(m, 1H, —ArH), 7.462~7.411(m, 1H, —ArH), 7.342~7.308(m, 1H, —ArH), 7.277~7.239(m, 1H, —ArH), 7.017~6.997(d, 1H, —ArH), 6.898~6.879(d, 1H, —ArH), 6.716(s, 1H, —CH═C), 4.671(s, 1H, —OH), 3.854(m, 1H, —CHO), 3.673~3.540(m, 7H, six-membered ring intra-CH$_2$N, amide N six-membered ring outer-CH$_2$, morpholine 2×—CH$_2$O), 3.124~3.077(q, 1H, amide N six-membered ring outer-CH$_2$—), 2.986~2.954(t, 2H, six-membered ring intra-CH$_2$), 2.402~2.392(m, 4H, morpholine-CH$_2$N, morpholine outer-CH$_2$N), 2.279~2.265(d, 2H, morpholine-CH$_2$N), 1.884(s, 3H, pyrrole-CH$_3$)

Example 4

(R,Z)-2-(5-Bromo-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one

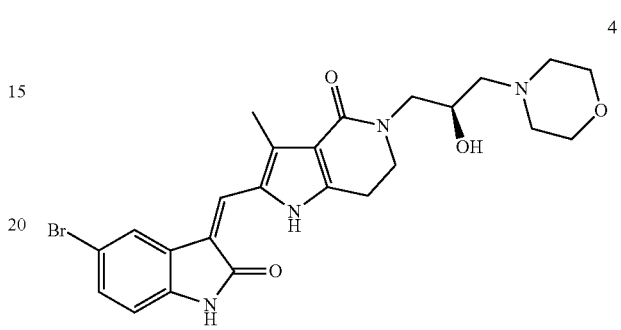

The title compound was prepared under the same conditions as described in step 6 of Example 1 with (R)-5-(2-hydroxy-3-morpholin-4-yl-propyl)-3-methyl-4-oxo-4,5,6,7-tetrahydro-1H-pyrrolo[3,2-c]pyridine-2-carbaldehyde 1f obtained from step 5 of Example 1 and 5-bromo-1,3-dihydro-indol-2-one as starting materials to give (R,Z)-2-(5-bromo-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 4 (24 mg, yield 50%) as a yellow solid.

MS m/z (ESI): 517.6[M+1]

$^1$HNMR (400 MHz, DMSO-d6): 13.723(s, 1H, pyrrole-NH), 11.047 (s, 1H, indole-NH), 8.131(s, 1H, —ArH), 7.820 (s, 1H, —CH═C), 7.292~7.271(dd, 1H, —ArH), 6.847~6.827(d, 1H, —ArH), 4.713~4.702(d, 1H, —OH), 3.897(m, 1H, —CHO), 3.626~3.569(t, 4H, morpholine 2×—CH$_2$O), 3.153~3.101(dd, 1H, amide N six-membered ring outer-CH$_2$—), 3.029~2.995(t, 2H, six-membered ring linked to pyrrole-CH$_2$—), 2.549 (s, 3H, pyrrole —CH$_3$), 2.308(t, 2H, morpholine-CH$_2$N)

Example 5

(S,Z)-2-(5-Fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one

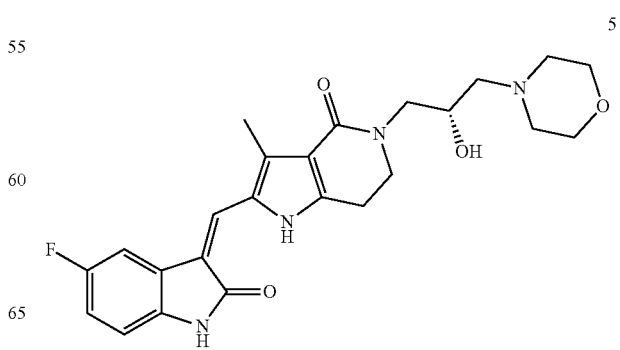

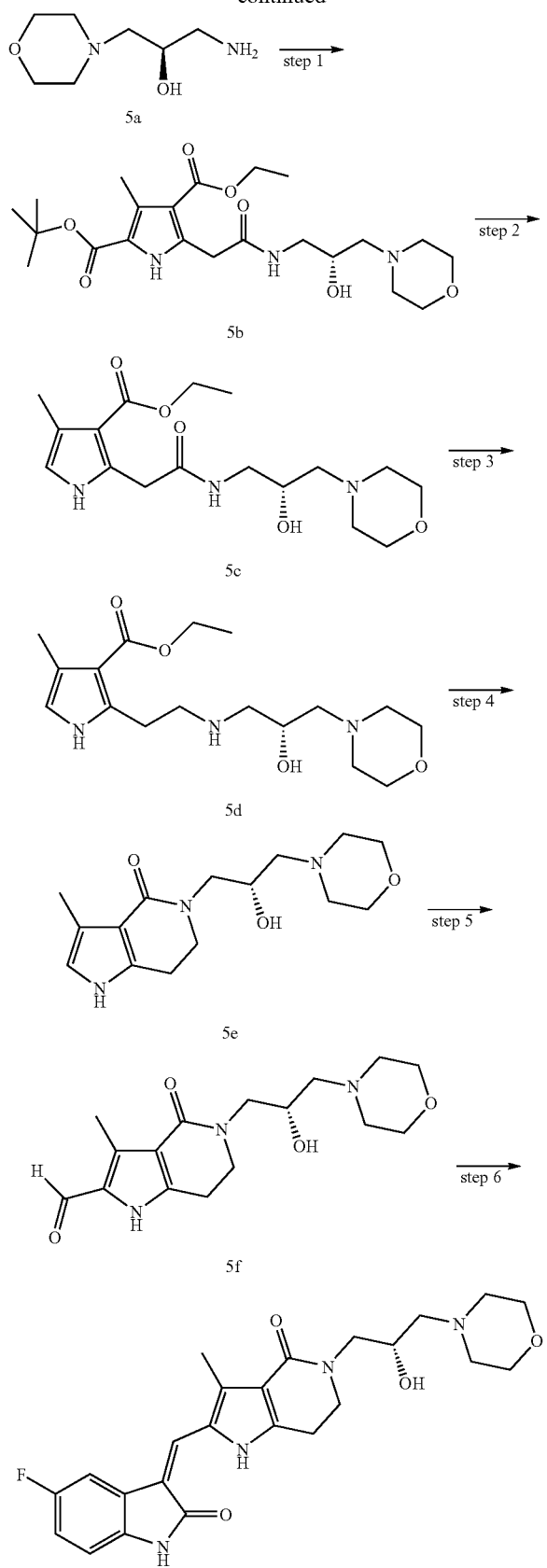

Step 1

5-[(2-Hydroxy-3-morpholin-4-yl-propylcarbamoyl)-methyl]-3-methyl-1H-pyrrole-2,4-dicarboxylic acid (R)-2-tert-butyl ester 4-ethyl ester (R)-1-Amino-3-morpholin-4-yl-propan-2-ol 5a (15.125 g, 94.5 mmol), 5-carboxymethyl-3-methyl-1H-pyrrole-2,4-dicarboxylic acid 2-tert-butyl ester 4-ethyl ester (32.34 g, 104 mmol), 1-hydroxybenzotriazol (25.5 g, 189.06 mmol) and N-ethyl-N'-(dimethylaminopropyl)-carbodiimide (36.2 g, 189.06 mmol) were dissolved in 450 mL of acetonitrile under stirring at room temperature. The reaction mixture was stirred at 50° C. in an oil bath for 3 hours. The reaction was completed until TLC showed the disappearance of starting materials. The solvent was evaporated under reduced pressure, and 150 mL of saturated brine was then added to the residue. The mixture was extracted with the solvent mixture of ethyl acetate and tetrahydrofuran (V:V=4:1, 200 mL ×5). The combined organic extracts were washed with saturated brine (100 mL), dried over anhydrous magnesium sulfate, filtered to remove the drying agent and concentrated to give an oil (75 g). The oil was purified by silica gel column chromatography to give the title compound 5-[(2-hydroxy-3-morpholin-4-yl-propylcarbamoyl)-methyl]-3-methyl-1H-pyrrole-2,4-dicarboxylic acid (R)-2-tert-butyl ester 4-ethyl ester 5b (30 g, yield 70%) as a light brown solid.

MS m/z (ESI): 454.4[M+1]

Step 2

(R)-2-[(2-Hydroxy-3-morpholin-4-yl-propylcarbamoyl)-methyl]-4-methyl-1H-pyrrole-3-carboxylic acid ethyl ester Under an argon atmosphere, 5-[(2-hydroxy-3-morpholin-4-yl-propylcarbamoyl)-methyl]-3-methyl-1H-pyrrole-2,4-dicarboxylic (R)-acid 2-tert-butyl ester 4-ethyl ester 5b (23 g, 50.77 mmol) was dissolved in 60 mL of anhydrous ethanol under stirring, and 63.5 mL of hydrochloric acid (12 N) was then added dropwise to the solution in an ice-water bath. Upon completion of the addition, the ice-water bath was removed, and the reaction system was stirred at 60° C. in an oil bath for 1.5 hours. The reaction was completed until TLC showed the disappearance of starting materials. The reaction system was adjusted to pH about 7 with 10N sodium hydroxide solution in a dry ice-acetone bath and lots of precipitates were formed. The mixture was filtered and the filter cake was washed with ethanol. The filtrate was concentrated under reduced pressure to remove the solvent, and the residue was adjusted to pH about 10 with sodium hydroxide solution (10N). The mixture was extracted with dichloromethane (150 mL×3). The combined organic extracts were washed with saturated brine (100 mL), dried over anhydrous magnesium sulfate, filtered to remove the drying agent and concentrated under reduced pressure to give the title compound (R)-2-[(2-hydroxy-3-morpholin-4-yl-propylcarbamoyl)-methyl]-4-methyl-1H-pyrrole-3-carboxylic acid ethyl ester 5c (14.6 g, yield 81.6%) as a yellow-green oil.

MS m/z (ESI): 354.8[M+1]

Step 3

(R)-2-[2-(2-Hydroxy-3-morpholin-4-yl-propylamino)-ethyl]-4-methyl-1H-pyrrole-3-carboxylic acid ethyl ester (R)-2-[(2-hydroxy-3-morpholin-4-yl-propylcarbamoyl)-methyl]-4-methyl-1H-pyrrole-3-carboxylic acid ethyl ester 5c (2.332 g, 6.6 mmol) was dissolved in 23 mL of anhydrous tetrahydrofuran under an argon atmosphere, and borane-tertrahydrofuran complex in tetrahydrofuran (23.12 mL, 1 mol/L, 23.12 mmol) was then added dropwise to the solution in an ice-water bath. Upon completion of the addition, the ice-water bath was removed. The reaction system was allowed to warm up to room temperature and refluxed at 95° C. in an oil bath for 1 hour. The reaction was completed until TLC showed the disappearance of starting materials. The solvent was evaporated under reduced pressure, and 5 mL of hydrochloric acid (2N) was then added to the residue. The mixture was stirred for 0.5 hour, and 5 mL of iced water was then added to the mixture. The mixture was adjusted to pH about 10 with 10N sodium hydroxide solution. The mixture was extracted with ethyl acetate (100 mL×2). The combined organic extracts were washed with saturated brine (50 mL), dried over anhydrous magnesium sulfate, filtered to remove the drying agent and concentrated under reduced pressure to give the title compound (R)-2-[2-(2-hydroxy-3-morpholin-4-yl-propylamino)-ethyl]-4-methyl-1H-pyrrole-3-carboxylic acid ethyl ester 5d (2.1 g, yield 93.75%) as a white solid.

MS m/z (ESI): 340.9[M+1]

Step 4

(S)-5-(2-Hydroxy-3-morpholin-4-yl-propyl)-3-methyl-1,5,6,7-tetrahydro-pyrrolo[3,2-c]pyridin-4-one (R)-2-[2-(2-Hydroxy-3-morpholin-4-yl-propylamino)-ethyl]-4-methyl-1H-pyrrole-3-carboxylic acid ethyl ester 5d (2.1 g, 6.2 mmol) and lithium hydroxide monohydrate (1.56 g, 37 mmol) were dissolved in 25 mL of glycol under stirring under an argon atmosphere. The reaction system was stirred at 140° C. in an oil bath for 50 minutes. The reaction was completed until TLC showed the disappearance of starting materials. After thin lay chromatography showed the starting material disappeared, the solvent was evaporated under reduced pressure, and 50 mL of saturated brine was then added to the residue. The mixture was extracted with dichloromethane (80 mL×3). The combined organic extracts were washed with saturated brine (80 mL), dried over anhydrous magnesium sulfate, filtered to remove the drying agent and concentrated under reduced pressure. The residue was purified by silica gel column chromatography to give the title compound (S)-5-(2-hydroxy-3-morpholin-4-yl-propyl)-3-methyl-1,5,6,7-tetrahydro-pyrrolo[3,2-c]pyridin-4-one 5e (610 g, yield 33.9%) as a white solid.

MS m/z (ESI): 294.5[M+1]

Step 5

(S)-5-(2-Hydroxy-3-morpholin-4-yl-propyl)-3-methyl-4-oxo-4,5,6,7-tetrahydro-1H-pyrrolo[3,2-c]pyridine-2-carbaldehyde Phosphorus oxychloride (500 μL, 1.3 mmol) and N,N-dimethylformamide (704 μL, 9 mmol) were dissolved in 15 mL of anhydrous dichloromethane under stirring at room temperature, and the reaction solution was stirring for 15 minutes while maintaining the temperature at −10° C. in an ice-water bath. (S)-5-(2-hydroxy-3-morpholin-4-yl-propyl)-3-methyl-1,5,6,7-tetrahydro-pyrrolo[3,2-c]pyridin-4-one 5e (586 mg, 2 mmol) was dissolved in 8 mL of dichloromethane under stirring, and the solution was then added dropwise to the above reaction system. Upon completion of the addition, the ice-water bath was removed. The reaction system was allowed to warm up to room temperature and stirred for another 2 hours. The reaction was completed until TLC showed the disappearance of starting materials. The reaction mixture was quenched with iced water and stirred for 15 minutes. The mixture was adjusted to pH about 12 with 10N sodium hydroxide solution. The mixture was extracted with the solvent mixture of dichloromethane and methanol (V:V=20:1, 100 mL×5). The combined organic extracts were washed with saturated brine (100 mL), dried over anhydrous magnesium sulfate, filtered to remove the drying agent and concentrated under reduced pressure. The residue was purified by silica gel column chromatography to give the title compound (S)-5-(2-hydroxy-3-morpholin-4-yl-propyl)-3-methyl-4-oxo-4,5,6,7-tetrahydro-1H-pyrrolo[3,2-c]pyridine-2-carbaldehyde 5f (490 mg, yield 78.8%) as a white solid.

MS m/z (ESI): 322.1[M+1]

Step 6

(S,Z)-2-(5-Fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one (S)-5-(2-Hydroxy-3-morpholin-4-yl-propyl)-3-methyl-4-oxo-4,5,6,7-tetrahydro-1H-pyrrolo[3,2-c]pyridine-2-carbaldehyde 5f (490 mg, 1.53 mmol), 5-fluoro-1,3-dihydro-indol-2-one (219 mg, 1.45 mmol) and piperidine (100 μL, 1.0 mmol) were dissolved in 5 mL of ethanol under stirring at room temperature. The reaction system was stirred at 80° C. in an oil bath in dark for 2 hours. The reaction was completed until TLC showed the disappearance of starting materials, and the oil bath was removed. The reaction mixture was naturally cooled down to room temperature to precipitate solids. The resulting solids were filtered to give the title compound (S,Z)-2-(5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 5 (460 mg, 69.9%) as a yellow solid.

MS m/z (ESI): 455.2[M+1]

$^1$HNMR (400 MHz, DMSO-d6): 13.674(s, 1H, pyrrole-NH), 10.945 (s, 1H, indole-NH), 7.771~7.800(m, 1H, —ArH), 7.762(s, 1H, —CH═C), 6.927~6.978(dd, 1H, —ArH), 6.842~6.874(d, 1H, —ArH), 4.707~4.719(d, 1H, —OH), 3.900~3.915(m, 1H, —CHO), 3.704~3.748(dd, 2H, amide N six-membered ring intra-CH$_2$—), 3.616~3.695(dd, 1H, amide N six-membered ring outer-CH$_2$—), 3.563~3.585 (t, 4H, morpholine 2×—CH$_2$O), 3.105~3.158(dd, 1H, amide N six-membered ring outer-CH$_2$—), 3.433(t, 2H, six-membered ring linked to pyrrole-CH$_2$—), 2.545(s, 3H, pyrrole-CH$_3$), 2.420~2.431(m, 2H, —CH$_2$N, morpholine intra-CH$_2$N), 2.420~2.431(m, 2H, —CH$_2$N, morpholine outer-CH$_2$N), 2.304~2.330(t, 2H, morpholine intra-CH$_2$N)

Example 6

(S,Z)-2-(5-Chloro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one

6

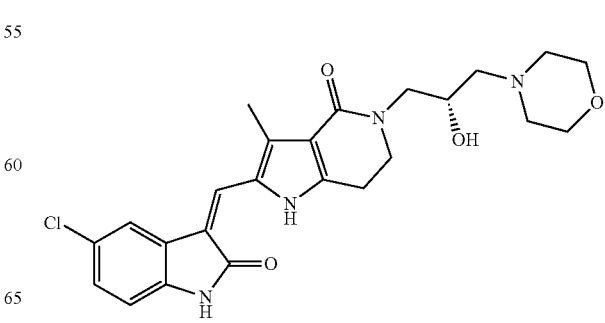

The title compound was prepared under the same conditions as described in step 6 of Example 5 with (S)-5-(2-hydroxy-3-morpholin-4-yl-propyl)-3-methyl-4-oxo-4,5,6,7-tetrahydro-1H-pyrrolo[3,2-c]pyridine-2-carbaldehyde 5f obtained from step 5 of Example 5 and 5-chloro-1,3-dihydro-indol-2-one as starting materials to give (S,Z)-2-(5-chloro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 6 (87 mg, yield 85%) as a yellow solid.

MS m/z (ESI): 471.6[M+1]

$^1$HNMR (400 MHz, DMSO-d6): 13.727(s, 1H, pyrrole-NH), 11.038 (s, 1H, indole-NH), 8.006~8.001(m, 1H, —ArH), 7.813(s, 1H, —CH=C), 7.166~7.140(dd, 1H, —ArH), 6.889~6.869(d, 1H, —ArH), 4.712~4.700(d, 1H, —OH), 3.893 (m, 1H, —CHO), 3.723~3.689(dd, 2H, amide N six-membered ring intra-CH$_2$—), 3.657~3.641(dd, 1H, amide N six-membered ring outer-CH$_2$—), 3.578~3.556(t, 4H, morpholine 2×—CH$_2$O), 3.152~3.099(dd, 1H, amide N six-membered ring outer-CH$_2$—), 3.026~2.993(t, 2H, six-membered ring linked to pyrrole-CH$_2$—), 2.547(s, 3H, pyrrole —CH$_3$), 2.424~2.412(m, 4H, —CH$_2$N, morpholine intra-CH$_2$N, morpholine outer-CH$_2$N), 2.311~2.290(t, 2H, morpholine intra-CH$_2$N)

Example 7

2-(Z)-[4-(2,3-Difluoro-phenyl)-2-oxo-1,2-dihydro-indol-3-ylidenemethyl]-5-[(S)-2-hydroxy-3-morpholin-4-yl-propyl]-3-methyl-1,5,6,7-tetrahydro-pyrrolo[3,2-c]pyridin-4-one

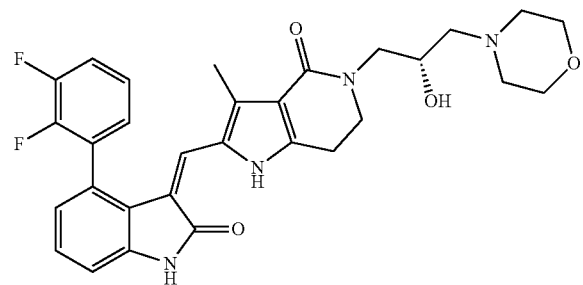

7

The title compound was prepared under the same conditions as described in step 6 of Example 5 with (S)-5-(2-hydroxy-3-morpholin-4-yl-propyl)-3-methyl-4-oxo-4,5,6,7-tetrahydro-1H-pyrrolo[3,2-c]pyridine-2-carbaldehyde 5f obtained from step 5 of Example 5 and 4-(2,3-difluoro-phenyl)-1,3-dihydro-indol-2-one 3d as starting materials to give 2-(Z)-[4-(2,3-difluoro-phenyl)-2-oxo-1,2-dihydro-indol-3-ylidenemethyl]-5-[(S)-2-hydroxy-3-morpholin-4-yl-propyl]-3-methyl-1,5,6,7-tetrahydro-pyrrolo[3,2-c]pyridin-4-one 7 (49 mg, yield 73%) as a red solid.

MS m/z (ESI): 549.2[M+1]

$^1$HNMR (400 MHz, DMSO-d6): 13.583(s, 1H, pyrrole-NH), 11.164 (s, 1H, indole-NH), 7.604~7.647(m, 1H, —ArH), 7.411~7.464(m, 1H, —ArH), 7.308~7.342(m, 1H, —ArH), 7.239~7.277(m, 1H, —ArH), 6.997~7.017(d, 1H, —ArH), 6.879~6.898(d, 1H, —ArH), 6.716(s, 1H, —CH=C), 4.671(s, 1H, —OH), 3.854(m, 1H, —CHO), 3.540~3.673(m, 7H, six-membered ring intra-CH$_2$N, amide N six-membered ring outer-CH$_2$, morpholine 2×—CH$_2$O), 3.095~3.124(g, 1H, amide N six-membered ring outer-CH$_2$—), 2.954~2.986(t, 2H, six-membered ring intra-CH$_2$), 2.392~2.402(m, 4H, morpholine-CH$_2$N, morpholine outer-CH$_2$N), 2.265~2.279(d, 2H, morpholine-CH$_2$N), 1.884(s, 3H, pyrrole-CH$_3$)

Example 8

(S,Z)-2-(5-bromo-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one

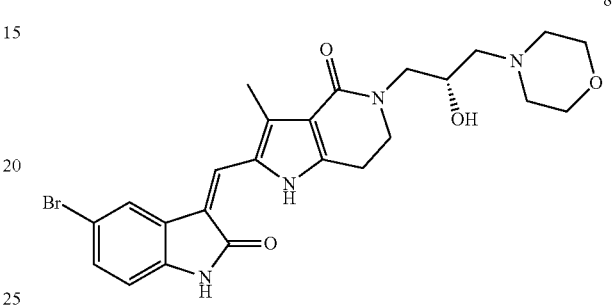

8

The title compound was prepared under the same conditions as described in step 6 of Example 5 with (S)-5-(2-hydroxy-3-morpholin-4-yl-propyl)-3-methyl-4-oxo-4,5,6,7-tetrahydro-1H-pyrrolo[3,2-c]pyridine-2-carbaldehyde 5f obtained from step 5 of Example 5 and 5-bromo-1,3-dihydro-indol-2-one as starting materials to give (S,Z)-2-(5-bromo-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 8 (49 mg, yield 78%) as a yellow solid.

MS in/z (ESI): 515.2[M+1]

$^1$HNMR (400 MHz, DMSO-d6): 13.720(s, 1H, pyrrole-NH), 11.042 (s, 1H, indole-NH), 8.127(s, 1H, —ArH), 7.813 (s, 1H, —CH=C), 7.290~7.265(dd, 1H, —ArH), 6.844~6.823(d, 1H, —ArH), 4.712~4.699(d, 1H, —OH), 3.907 (m, 1H, —CHO), 3.578~3.555(t, 4H, morpholine 2×—CH$_2$O), 3.151~3.098(dd, 1H, amide N six-membered ring outer-CH$_2$—), 3.025~2.992(t, 2H, six-membered ring linked to pyrrole-CH$_2$—), 2.547(s, 3H, pyrrole —CH$_3$), 2.306~2.290(t, 2H, morpholine intra-CH$_2$N)

Example 9

(S,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-acetamide

9

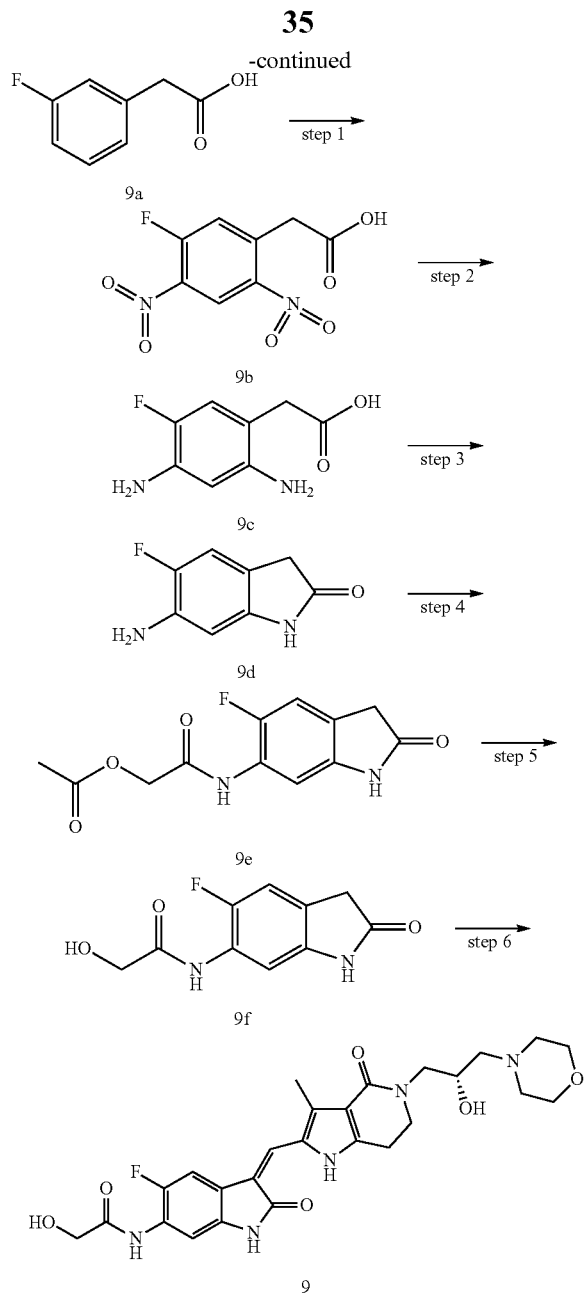

Step 1

(5-Fluoro-2,4-dinitro-phenyl)-acetic acid (3-Fluoro-phenyl)-acetic acid 9a (31.5 g, 0.204 mol) was added to 64 mL of sulfuric acid (98%) at room temperature, and 100 mL of the solvent mixture of nitric acid (65%-68%) and sulfuric acid (98%) (V:V=1:1) was added dropwise to the solution while maintaining the temperature at 35° C. Upon completion of the addition, the reaction mixture was stirred at 35° C. The reaction was completed until TLC showed the disappearance of starting materials. Ice was added to the reaction mixture and the mixture was filtered after ice-out to give the title compound (5-fluoro-2,4-dinitro-phenyl)-acetic acid 9b (49 mg) as a light yellow oil.

MS m/z (ESI): 243.5[M−1]

Step 2

(2,4-Diamino-5-fluoro-phenyl)-acetic acid (5-Fluoro-2,4-dinitro-phenyl)-acetic acid 9b (10 g, 38.7 mmol) was dissolved in 150 mL of methanol under stirring at room temperature, and palladium on activated carbon (5%, 1.5 g) was then added to the solution. The reaction mixture was hydrogenated under 0.3 Mpa of hydrogen. The reaction was completed until TLC showed the disappearance of starting materials. The above mixture was filtered twice and the filtrate was concentrated under reduced pressure to give the title compound (2,4-diamino-5-fluoro-phenyl)-acetic acid 9c (7.12 g) as a brown solid which was directly used in the further reaction.

Step 3

6-Amino-5-fluoro-indol-2-one (2,4-Diamino-5-fluoro-phenyl)-acetic acid 9c (7.12 g, 38.7 mmol) was dissolved in 100 mL of hydrochloric acid (1 M) under stirring at room temperature, and the reaction solution was heated to reflux for 1 hour. The reaction was completed until TLC showed the disappearance of starting materials. The reaction mixture was naturally cooled down to room temperature, followed by an ice-water bath cooling, and 100 mL of sodium hydroxide solution (1M) was then added dropwise to neutralize the reaction solution. The mixture was extracted with ethyl acetate (125 mL ×4). The combined organic extracts were washed with saturated brine (100 mL), dried over anhydrous magnesium sulfate, filtered and concentrated under reduced pressure to give the title compound 5-fluoro-6-amino-1,3-dihydro-indol-2-one 9d (5.3 g, yield 82.8%) as a yellow solid.

MS m/z (ESI): 165.3[M−1]

Step 4

Acetic acid (5-fluoro-2-oxo-2,3-dihydro-1H-indol-6-ylcarbamoyl)-methyl ester 5-Fluoro-6-amino-indol-2-one 9d (500 mg, 3.0 mmol) was dissolved in 10 mL of tetrahydrofuran under stirring at room temperature, and 0.4 mL of pyridine was then added to the solution. After stirring to mix well, the reaction system was cooled down to −40° C. in a dry ice-acetone bath. Chlorocarbonylmethyl ester (420 mg, 3.0 mmol) was dissolved in 10 mL of tetrahydrofuran, and the solution was then added dropwise to the above reaction system. Upon completion of the addition, the dry ice-acetone bath was removed. The reaction system was allowed to warm up to room temperature and stirred overnight until TLC showed the disappearance of starting materials. The reaction mixture was filtered, and the filter cake was washed with water thrice to give the title compound acetic acid (5-fluoro-2-oxo-2,3-dihydro-1H-indol-6-ylcarbamoyl)-methyl ester 9e (562 mg, yield 70.4%) as a gray solid.

MS: 265.3[M−1]

Step 5

N-(5-Fluoro-2-oxo-2,3-dihydro-1H-indol-6-yl)-2-hydroxy-acetamide

Acetic acid (5-fluoro-2-oxo-2,3-dihydro-1H-indol-6-ylcarbamoyl)-methyl ester 9e (58 mg, 0.22 mmol) was dissolved in 1 mL of methanol under stirring at room temperature, and 1 mL of water and sodium hydroxide (15 mg, 0.375 mmol) were then added to the solution. Upon completion of the addition, the reaction mixture was stirred for another 1 hour. The reaction was completed until TLC showed the disappearance of starting materials. The above mixture was filtered, the filter cake was washed with water thrice and dried to give the title compound N-(5-fluoro-2-oxo-2,3-dihydro-1H-indol-6-yl)-2-hydroxy-acetamide 9f (46 mg, yield 93.8%) as a gray solid.

MS: 223.7[M−1]

Step 6

(S,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-acetamide (S)-5-(2-Hydroxy-3-morpholin-4-yl-propyl)-3-methyl-4-oxo-4,5,6,7-tetrahydro-1 H-pyrrolo[3,2-c]pyridine-2-carbaldehyde 5f (40 mg, 0.125 mmol) was dissolved in 2 mL of ethanol under stirring at room temperature, and N-(5-fluoro-2-oxo-2,3-dihydro-1H-indol-6-yl)-2-hydroxy-acetamide 9f (25.1 mg, 0.112 mmol) was then added to the solution. Upon completion of the addition, the mixture was stirred until all dissolved, and piperidine (50 μL, 0.5 mmol) was then added to the reaction solution. Upon completion of the addition, the reaction system was stirred at 80° C. in an oil bath in dark for 2 hours. The reaction was completed until TLC showed the disappearance of starting materials, and the oil bath was removed. The reaction system was naturally cooled down to room temperature to precipitate solids. The resulting solids were filtered to give the title compound (S,Z)-N-{5-fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-acetamide 9 (51 mg, yield 80%) as a yellow solid.

MS m/z (ESI): 528.3[M+1]

Example 10

(S,Z)-2-[5-Fluoro-6-(4-fluoro-benzylamino)-2-oxo-1,2-dihydro-indol-3-ylidenemethyl]-5-(2-hydroxy-3-morpholin-4-yl-propyl)-3-methyl-1,5,6,7-tetrahydro-pyrrolo[3,2-c]pyridin-4-one

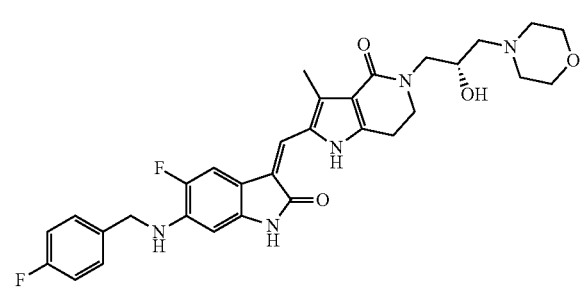

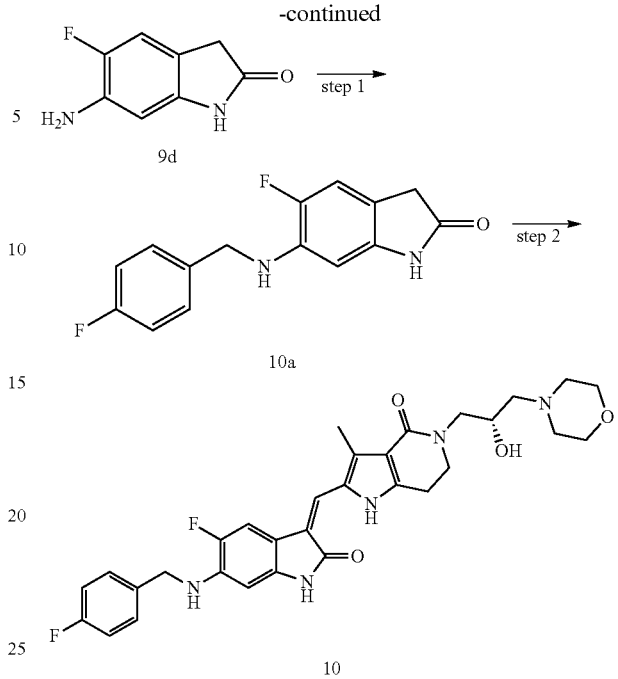

Step 1

5-Fluoro-6-(4-methyl-benzylamino)-1,3-dihydro-indol-2-one

5-Fluoro-6-Amino-1,3-dihydro-indol-2-one 9d(2.26 g, 13.6 mmol) was dissolved in 40 mL of ethanol under stirring at room temperature. The solution was cooled down to 0° C. in an ice-water bath, and 4-fluoro-benzaldehyde (1.5 mL, 13.6 mmol) was then added to the solution. Upon completion of the addition, the reaction mixture was stirred at room temperature for 1 hour, and sodium borohydride (1.08 g, 28.5 mmol) was then added to the mixture. The reaction mixture was refluxed for 18 hours. The reaction mixture was naturally cooled down to room temperature, and iced water was added to precipitate solids. The resulting solids were filtered. The filter cake was washed with water (50 mL ×3), and purified by silica gel column chromatography to give the title compound 5-fluoro-6-(4-methyl-benzylamino)-1,3-dihydro-indol-2-one 10a (1.67 g, 45%) as a white solid.

MS m/z (ESI): 275[M+1]

Step 2

(S,Z)-2-[5-Fluoro-6-(4-fluoro-benzylamino)-2-oxo-1,2-dihydro-indol-3-ylidenemethyl]-5-(2-hydroxy-3-morpholin-4-yl-propyl)-3-methyl-1,5,6,7-tetrahydro-pyrrolo[3,2-c]pyridin-4-one (S)-5-(2-Hydroxy-3-morpholin-4-yl-propyl)-3-methyl-4-oxo-4,5,6,7-tetrahydro-1 H-pyrrolo[3,2-c]pyridine-2-carbaldehyde 5f (40 mg, 0.125 mmol) was dissolved in 2 mL of ethanol under stirring at room temperature, and 5-fluoro-6-(4-methyl-benzylamino)-1,3-dihydro-indol-2-one 10a (30.7 mg, 0.112 mmol) was then added to the solution. Upon completion of the addition, the reaction mixture was stirred until all dissolved, and piperidine (0.05 mL, 0.5 mmol) was then added to reaction solution. Upon completion of the addition, the reaction mixture was refluxed in an oil bath for 2 hours. The reaction was completed until TLC showed the disappearance of starting materials, and the reaction mixture was naturally cooled down to room temperature, filtered under reduced pressure to give the title compound (S,Z)-2-[5-fluoro-6-(4-fluoro-benzylamino)-2-oxo-1,2-dihydro-indol-3-ylidenemethyl]-5-(2-hydroxy-3-morpholin-4-yl-propyl)-3-methyl-1,5,6,7-tetrahydro-pyrrolo[3,2-c]pyridin-4-one 10 (18 mg, 27.8%) as a gray solid.

MS m/z (ESI): 578.6[M+1]

¹HNMR (400 MHz, DMSO-d6): 13.503 (s, 1H, pyrrole-NH), 10.557 (s, 1H, indole-NH), 7.584~7.614(d, 1H, —ArH), 7.359~7.400(m, 2H, —ArH), 7.359 (s, 1H, —CH=C), 7.140~7.184(t, 2H, —ArH), 6.426(m, 1H, —NH), 6.039~6.057 (d, 1H, —ArH), 4.684~4.696(d, 1H, —OH), 4.346~4.361(d, 2H, —C=CCH₂N), 3.893(m, 1H, —CHO), 3.667~3.713(d, 2H, six-membered ring intra-CH₂N), 3.596~3.627(q, 1H, amide N six-membered ring outer-CH₂—), 3.564(t, 4H, morpholine 2x—CH₂O), 3.07~3.12(q, 1H, amide N six-membered ring outer-CH₂—), 2.928~2.961(t, 2H, six-membered ring intra-CH₂), 2.468(s, 3H, pyrrole-CH₃), 2.417(m, 4H, morpholine-CH₂N, morpholine outer-CH₂N), 2.297 (m, 2H, morpholine-CH₂N)

Example 11

(S,Z)-N-{5-Fluoro-3[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide

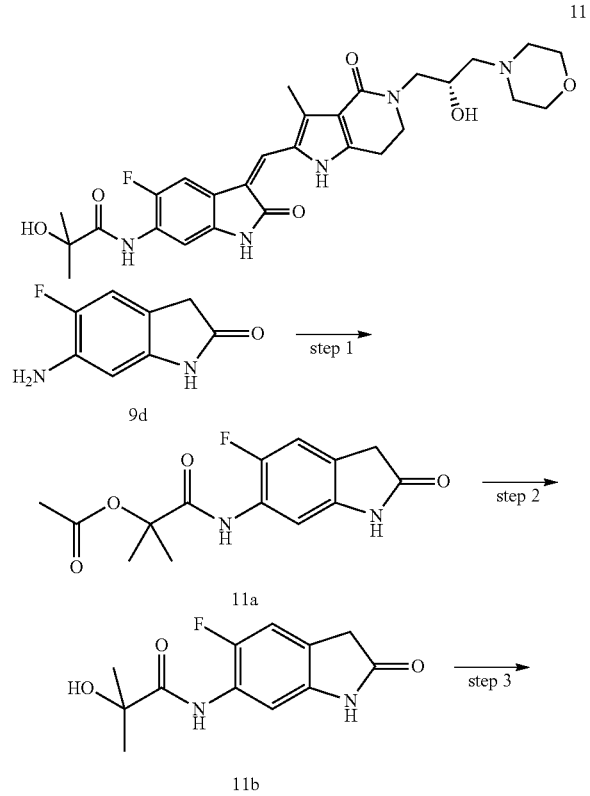

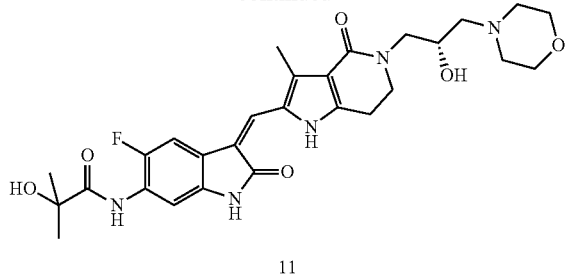

11

Step 1

Acetic acid 1-(5-fluoro-2-oxo-2,3-dihydro-1H-indol-6-ylcarbamoyl)-1-methyl-ethyl ester 5-Fluoro-6-Amino-indol-2-one 9d (410 mg, 2.47 mmol) was dissolved in 10 mL of tetrahydrofuran under stirring at room temperature, the solution was cooled down to −45° C. in a dry ice-acetone bath, and 332 μL of pyridine was then added to the solution. 2-acetoxy isoburyryl chloride (423 mg, 2.71 mmol) was dissolved in 10 mL of tetrahydrofuran, and the solution was then added dropwise to the above reaction solution. Upon completion of the addition, the dry ice-acetone bath was removed. The reaction system was allowed to warm up to room temperature and stirred overnight. The reaction was completed until TLC showed the disappearance of starting materials. The reaction mixture was filtered, and the filter cake was washed with water and dried to give the title compound acetic acid 1-(5-fluoro-2-oxo-2,3-dihydro-1H-indol-6-ylcarbamoyl)-1-methyl-ethyl ester 11a (792 mg) as a white solid which was directly used in the further reaction.

MS m/z (ESI): 293.7[M−1]

Step 2

N-(5-Fluoro-2-oxo-2,3-dihydro-1H-indol-6-yl)-2-hydroxy-2-methyl-propionamide

Acetic acid 1-(5-fluoro-2-oxo-2,3-dihydro-1H-indol-6-ylcarbamoyl)-1-methyl-ethyl ester 11a (2.035 mg, 6.9 mmol) was dissolved in 20 mL of methanol under stirring at room temperature, and 20 mL of sodium hydroxide solution (0.7 M) was then added to the solution. The reaction solution was stirred for 4 hours. The reaction was completed until TLC showed the disappearance of starting materials, and the above solution was neutralized with hydrochloric acid (1 M) and the solvent was evaporated under reduced pressure. The residue was purified by silica gel column chromatography and dried to give N-(5-fluoro-2-oxo-2,3-dihydro-1H-indol-6-yl)-2-hydroxy-2-methyl-propionamide 11b (900 mg, yield 59.2%) as a white solid.

MS m/z (ESI): 253.6[M+1]

Step 3

(S,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide (S)-5-(2-Hydroxy-3-morpholin-4-yl-propyl)-3-methyl-4-oxo-4,5,6,7-tetrahydro-1H-pyrrolo[3,2-c]pyridine-2-carbaldehyde 5f (40 mg, 0.125 mmol), N-(5-fluoro-2-oxo-2,3-dihydro-1H-indol-6-yl)-2-hydroxy-2-methyl-propionamide 11b (28.3 mg, 0.112 mmol) and piperidine (50 µL, 0.5 mmol) were dissolved in 2 mL of ethanol under stirring at room temperature. The reaction system was stirred at 80° C. in an oil bath in dark for 2 hours. The reaction was completed until TLC showed the disappearance of starting materials, and the oil bath was removed. The reaction system was naturally cooled down to room temperature to precipitate solids. The resulting solids were filtered to give the title compound (S,Z)-N-{5-fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide 11 (46 mg, 74%) as a yellow solid.

MS m/z (ESI): 556.9[M+1]

$^1$HNMR (400 MHz, DMSO-d6): 13.656(s, 1H, pyrrole-NH), 10.951 (s, 1H, indole-NH), 9.282(s, 1H, —NHCO), 7.873~7.901(d, 1H, —ArH), 7.778~7.794 (m, 1H, —ArH), 7.670(s, 1H, —CH=C), 6.052(s, 1H, —OHC(CH$_3$)$_2$), 4.698 (d, 1H, OH), 3.893(m, 1H, —CHO), 3.667~3.713(d, 2H, six-membered ring intra-CH$_2$N), 3.596~3.627(q, 1H, amide N six-membered ring outer-CH$_2$-), 3.557~3.578(t, 4H, morpholine 2×—CH$_2$O), 3.09~3.125(q, 1H, amide N six-membered ring outer-CH$_2$—), 2.961~3.012(t, 2H, six-membered ring intra-CH$_2$), 2.524(s, 3H, pyrrole-CH$_3$), 2.412~2.424(m, 4H, morpholine-CH$_2$N, morpholine outer-CH$_2$N), 2.297~2.308(m, 2H, morpholine-CH$_2$N), 1.376(s, 6H, 2×—CH$_3$)

Example 12

(S,Z)-2-(7-Bromo-5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one

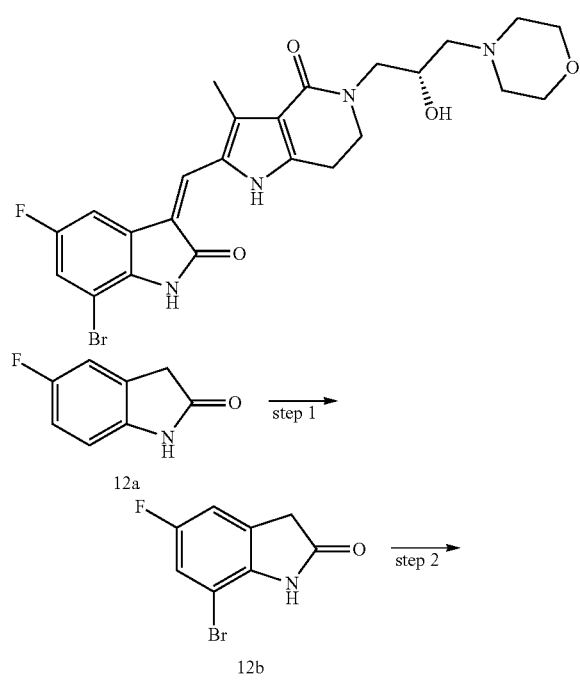

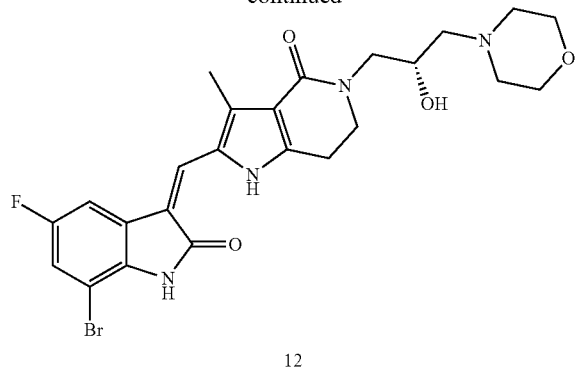

12

Step 1

7-Bromo-5-fluoro-1,3-dihydro-indol-2-one

5-Fluoro-1,3-dihydro-indol-2-one 12a (1.5 g, 0.01 mmol) was dissolved in 15 mL of acetonitrile under stirring at room temperature, and N-bromosuccinimide (1.8 g, 0.01 mmol) was then added dropwise to the solution. Upon completion of the addition, the reaction mixture was stirred overnight and lots of precipitates were formed. The reaction was completed until TLC showed the disappearance of starting materials, and the reaction mixture was filtered to give 7-bromo-5-fluoro-1,3-dihydro-indol-2-one 12b (2 g, 87%) as a gray solid.

MS m/z (ESI): 228.3[M−1]

Step 2

(S,Z)-2-(7-Bromo-5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one (S)-5-(2-Hydroxy-3-morpholin-4-yl-propyl)-3-methyl-4-oxo-4,5,6,7-tetrahydro-1H-pyrrolo[3,2-c]pyridine-2-carbaldehyde 5f (40 mg, 0.125 mmol) was dissolved in 2 mL of ethanol under stirring at room temperature, and 7-bromo-5-fluoro-1,3-dihydro-indol-2-one 12b (25.8 mg, 0.112 mmol) was then added to the solution. Upon completion of the addition, the reaction mixture was stirred until all dissolved, and piperidine (0.05 mL, 0.5 mmol) was then added to the solution. Upon completion of the addition, the reaction mixture was heated to reflux in an oil bath for 2 hours. The reaction was completed until TLC showed the disappearance of starting materials, and the reaction mixture was naturally cooled down to room temperature, and filtered under reduced pressure to give the title compound (S,Z)-2-(7-bromo-5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 12 (45 mg, 75.4%) as a yellow solid.

MS m/z (ESI): 533.6[M+1]

$^1$HNMR (400 MHz, DMSO-d6): 13.689(s, 1H, pyrrole-NH), 11.196 (s, 1H, indole-NH), 7.860~7.866(d, 1H, —ArH), 7.784(s, 1H, —CH=C), 7.232~7.260(m, 1H, —ArH), 4.703~4.716(d, 1H, —OH), 3.896~2.909(m, 1H, —CHO), 3.631~3.747(m, 3H, six-membered ring intra-CH$_2$N, amide N six-membered ring outer-CH$_2$—), 3.555~3.578(t, 4H, morpholine 2×—CH$_2$O), 3.097~3.150(q, 1H, amide N six-membered ring outer-CH$_2$—), 3.015~3.048 (t, 2H, six-membered ring intra-CH$_2$), 2.548(s, 3H, pyrrole-CH$_3$), 2.411~2.424(m, 4H, morpholine-CH$_2$N, morpholine outer-CH$_2$N), 2.291~2.307(m, 2H, morpholine-CH$_2$N)

Example 13

(S,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide

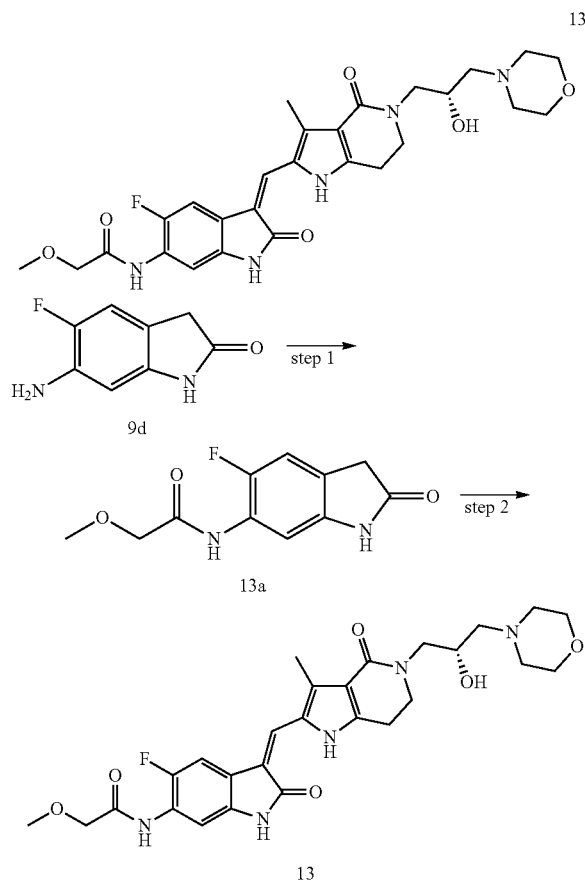

Step 1

5-Fluoro-6-methoxyacetamido-2-oxoindole

5-Fluoro-6-Amino-indol-2-one 9d (2.028 g, 12.2 mmol) was dissolved in 30 mL of tetrahydrofuran under stirring at room temperature, and 1.3 mL of pyridine was then added to the solution. The reaction system was cooled down to –50° C. in a dry ice-ethanol bath. Methoxy-acetyl chloride (1.35 g, 12.5 mmol) was dissolved in 20 mL of tetrahydrofuran under stirring, and the solution was then added dropwise to the above reaction system. Upon completion of the addition, the dry ice-ethanol bath was removed. The reaction system was allowed to warm up to room temperature and stirred overnight until TLC showed the disappearance of starting materials. The resulting solid was filtered, washed with water (10 mL ×3) and recrystallized from methanol to give the title compound 5-fluoro-6-methoxyacetamido-2-oxoindole 13a (1.18 g, yield 40.6%) as a gray solid.

MS m/z (ESI): 239.3[M+1]

Step 2

(S,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide (S)-5-(2-Hydroxy-3-morpholin-4-yl-propyl)-3-methyl-4-oxo-4,5,6,7-tetrahydro-1H-pyrrolo[3,2-c]pyridine-2-carbaldehyde 5f (40 mg, 0.125 mmol) was dissolved in 2 mL of ethanol under stirring at room temperature, and 5-fluoro-6-methoxyacetamido-2-oxoindole 13a (26.7 mg, 0.112 mmol) was then added to the solution. Upon completion of the addition, the reaction mixture was stirred until all dissolved, and piperidine (0.05 mL, 0.5 mmol) was then added to the solution. Upon completion of the addition, the reaction mixture was heated to reflux in an oil bath for 2 hours. The reaction was completed until TLC showed the disappearance of starting materials. The reaction mixture was naturally cooled down to room temperature, and filtered under reduced pressure to give the title compound (S,Z)-N-{5-fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide 13 (52 mg, yield 85.8%) as a yellow solid.

MS m/z (ESI): 542.2[M+1]

$^1$HNMR (400 MHz, DMSO-d6): 13.666(s, 1H, pyrrole-NH), 10.919 (s, 1H, indole-NH), 9.313(s, 1H, —NHCO), 7.841~7.869(d, 1H, —ArH), 7.672(s, 1H, —CH=C), 7.546~7.562(m, 1H, —ArH), 4.703~4.716(d, 1H, —OH), 4.062(s, 2H, —CH$_2$O), 3.896~2.909(m, 1H, —CHO), 3.652~3.720(m, 3H, six-membered ring intra-CH$_2$N, amide N six-membered ring outer-CH$_2$—), 3.556~3.578(t, 4H, morpholine 2×—CH$_2$O), 3.404(s, 3H, —CH$_3$O), 3.097~3.150(q, 1H, amide N six-membered ring outer-CH$_2$—), 2.982~3.015 (t, 2H, six-membered ring intra-CH$_2$), 2.523(s, 3H, pyrrole-CH$_3$), 2.414~2.425(m, 4H, morpholine-CH$_2$N, morpholine outer-CH$_2$N), 2.291~2.307(m, 2H, morpholine-CH$_2$N)

Example 14

(R,Z)-2-(7-Bromo-5-fluoro-2-oxo-1,2-dihydro-indol-3-ylidenemethyl)-5-(2-hydroxy-3-morpholin-4-yl-propyl)-3methyl-1,5,6,7-tetrahydro-pyrrolo[3,2-c]pyridin-4-one

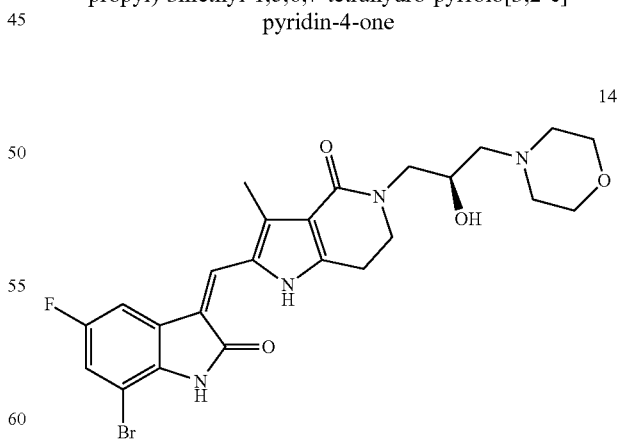

The title compound was prepared under the same conditions as described in step 6 of Example 1 with (R)-5-(2-hydroxy-3-morpholin-4-yl-propyl)-3-methyl-4-oxo-4,5,6,7-tetrahydro-1H-pyrrolo[3,2-c]pyridine-2-carbaldehyde 1f obtained from step 5 of Example 1 and 7-bromo-5-fluoro-1,3-dihydro-indol-2-one 12b as starting materials to give (R,Z)-

2-(7-bromo-5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 14 (20 mg, yield 40%) as a yellow solid.

MS m/z (ESI): 533.6[M+1]

¹HNMR (400 MHz, DMSO-d6): 13.691(s, 1H, pyrrole-NH), 11.204(s, 1H, indole-NH), 7.874~7.851(d, 1H, ~ArH), 7.797(s, 1H, —CH=C), 7.269~7.243(m, 1H, —ArH), 4.710~4.698(d, 1H, —OH), 3.900~3.890(m, 1H, —CHO), 3.759~3.611(m, 3H, six-membered ring intra-CH$_2$N, amide N six-membered ring outer-CH$_2$—), 3.572~3.550(t, 4H, morpholine 2×—CH$_2$O), 3.148~3.095(q, 1H, amide N six-membered ring outer-CH$_2$—), 3.047~3.014(t, 2H, six-membered ring intra-CH$_2$), 2.548(s, 3H, pyrrole-CH$_3$), 2.418~2.323(m, 4H, morpholine-CH$_2$N, morpholine outer-CH$_2$N), 2.302~2.285(m, 2H, morpholine-CH$_2$N)

Example 15

(R,Z)-2-[5-Fluoro-6-(4-fluoro-benzylamino)-2-oxo-1,2-dihydro-indol-3-ylidenemethyl]-5-(2-hydroxy-3-morpholin-4-yl-propyl)-3-methyl-1,5,6,7-tetrahydro-pyrrolo[3,2-c]pyridin-4-one

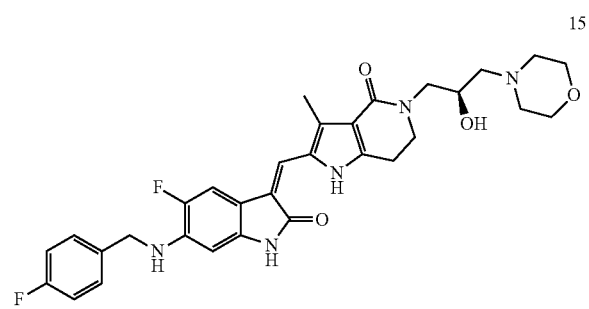

The title compound was prepared under the same conditions as described in step 6 of Example 1 with (R)-5-(2-hydroxy-3-morpholin-4-yl-propyl)-3-methyl-4-oxo-4,5,6,7-tetrahydro-1H-pyrrolo[3,2-c]pyridine-2-carbaldehyde 1f obtained from step 5 of Example 1 and 5-fluoro-6-(4-methyl-benzylamino)-1,3-dihydro-indol-2-one 10a as starting materials to give (R,Z)-2-[5-fluoro-6-(4-fluoro-benzylamino)-2-oxo-1,2-dihydro-indol-3-ylidenemethyl]-5-(2-hydroxy-3-morpholin-4-yl-propyl)-3-methyl-1,5,6,7-tetrahydro-pyrrolo[3,2-c]pyridin-4-one 15 (53 mg, yield 65.6%) as a crimson solid.

MS m/z (ESI): 578.7[M+1]

¹HNMR (400 MHz, DMSO-d6): 13.504(s, 1H, pyrrole-NH), 10.558(s, 1H, indole-NH), 7.614~7.585(d, 1H, —ArH), 7.400~7.379(m, 2H, —ArH), 7.359(s, 1H, —CH=C), 7.140~7.191(t, 2H, —ArH), 6.431(m, 1H, —NH), 6.058~6.040(d, 1H, —ArH), 4.698~4.686(d, 1H, —OH), 4.346~4.361(d, 2H, —C=CCH$_2$N), 3.894(m, 1H, —CHO), 3.731~3.668(d, 2H, six-membered ring intra-CH$_2$N), 3.644~3.612(q, 1H, amide N six-membered ring outer-CH$_2$—), 3.596~3.553(t, 4H, morpholine 2×—CH$_2$O), 3.135~3.082(g, 1H, amide N six-membered ring outer-CH$_2$—), 2.928~2.961(t, 2H, six-membered ring intra-CH$_2$), 2.468(s, 3H, pyrrole-CH$_3$), 2.419~2.408(m, 4H, morpholine-CH$_2$N, morpholine outer-CH$_2$N), 2.299~2.289(m, 2H, morpholine-CH$_2$N)

Example 16

(R,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide

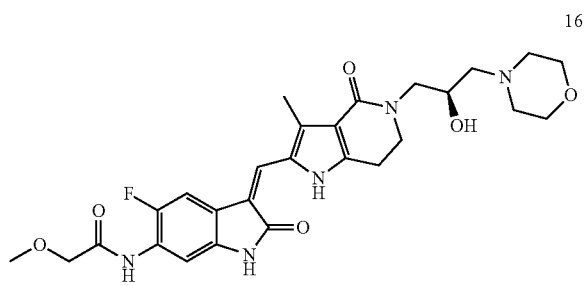

The title compound was prepared under the same conditions as described in step 6 of Example 1 with (R)-5-(2-hydroxy-3-morpholin-4-yl-propyl)-3-methyl-4-oxo-4,5,6,7-tetrahydro-1H-pyrrolo[3,2-c]pyridine-2-carbaldehyde 1f obtained from step 5 of Example 1 and 5-fluoro-6-methoxy-acetamido-2-oxoindole 13a as starting materials to give (R,Z)-N-{5-fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide 16 (60 mg, yield 87%) as a yellow solid.

MS m/z (ESI): 543.0[M+1]

¹HNMR (400 MHz, DMSO-d6): 13.668(s, 1H, pyrrole-NH), 10.923(s, 1H, indole-NH), 9.320(s, 1H, —NHCO), 7.875~7.847(d, 1H, —ArH), 7.678(s, 1H, —CH=C), 7.562~7.546(m, 1H, —ArH), 4.711~4.699(d, 1H, —OH), 4.063(s, 2H, —CH$_2$O), 3.729~3.653(m, 3H, six-membered ring intra-CH$_2$N, amide N six-membered ring outer-CH$_2$—), 3.579~3.556(t, 4H, morpholine 2×—CH$_2$O), 3.404(s, 3H, —CH$_3$O), 2.983~3.017(t, 2H, six-membered ring intra-CH$_2$), 2.525(s, 3H, pyrrole-CH$_3$), 2.412~2.424(m, 4H, morpholine-CH$_2$N, morpholine outer-CH$_2$N), 2.289~2.306(m, 2H, morpholine-CH$_2$N)

Example 17

(R,Z)-N-{5-Fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide

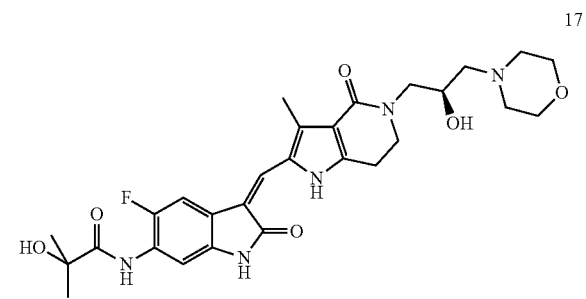

The title compound was prepared under the same conditions as described in step 6 of Example 1 with (R)-5-(2-hydroxy-3-morpholin-4-yl-propyl)-3-methyl-4-oxo-4,5,6,7-tetrahydro-1H-pyrrolo[3,2-c]pyridine-2-carbaldehyde 1f obtained from step 5 of Example 1 and N-(5-fluoro-2-oxo-2,3-dihydro-1H-indol-6-yl)-2-hydroxy-2-methyl-propionamide 11b as starting materials to give (R,Z)-N-{5-fluoro-3-[5-(2-hydroxy-3-morpholin-4-yl-propyl)-3-methyl-4-oxo-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide 17 (71 mg, yield 82%) as a yellow solid.

MS m/z (ESI): 556.2[M+1]

¹HNMR (400 MHz, DMSO-d6): 13.658(s, 1H, pyrrole-NH), 10.954(s, 1H, indole-NH), 9.289(s, 1H, —NHCO), 7.875~7.903(d, 1H, —ArH), 7.796~7.780(m, 1H, —ArH), 7.672(s, 1H, —CH═C), 6.055(s, 1H, —OHC(CH₃)₂), 4.701 (d, 1H, OH), 3.722(m, 1H, —CHO), 3.655~3.691(d, 2H, six-membered ring intra-CH₂N), 3.639(q, 1H, amide N six-membered ring outer-CH₂—), 3.559~3.580(t, 4H, morpholine 2×—CH₂O), 2.986~3.019(t, 2H, six-membered ring intra-CH₂), 2.526(s, 3H, pyrrole-CH₃), 2.415~2.425(m, 4H, morpholine-CH₂N, morpholine outer-CH₂N), 2.299~2.309 (m, 2H, morpholine-CH₂N), 1.378(s, 6H, 2×—CH₃)

Example 18

(R,Z)-5-(2-Hydroxyl-3-morpholin-4-yl-propyl)-3-methyl-2-(2-oxo-4-pyridin-4-yl-1,2-dihydro-indol-3-ylidenemethyl)-1,5,6,7-tetrahydro-pyrrolo[3,2-c]pyridin-4-one

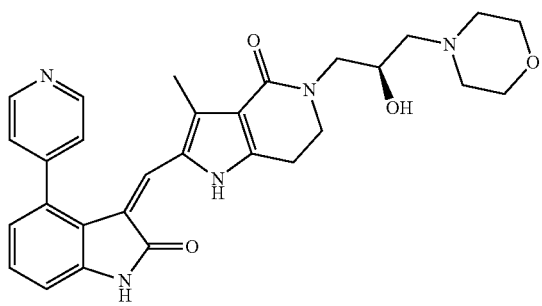

18

The title compound was prepared under the same conditions as described in step 6 of Example 1 with (R)-5-(2-hydroxy-3-morpholin-4-yl-propyl)-3-methyl-4-oxo-4,5,6,7-tetrahydro-1H-pyrrolo[3,2-c]pyridine-2-carbaldehyde 1f obtained from step 5 of Example 1 and 4-pyridin-4-yl-1,3-dihydro-indol-2-one as starting materials to give (R,Z)-5-(2-hydroxy-3-morpholin-4-yl-propyl)-3-methyl-2-(2-oxo-4-pyridin-4-yl-1,2-dihydro-indol-3-ylidenemethyl)-1,5,6,7-tetrahydro-pyrrolo[3,2-c]pyridin-4-one 18 (58 mg, yield 72.5%) as a yellow solid.

MS m/z (ESI): 514.2[M+1]

¹HNMR (400 MHz, DMSO-d6): 13.573(s, 1H, pyrrole-NH), 11.149(s, 1H, indole-NH), 7.742~7.770(d, 2H, pyridine N—CH═), 7.500~7.513(d, 2H, pyridine —CH═), 7.226~7.265(t, 1H, —ArH), 6.976~6.995(t, 1H, —ArH), 6.813~6.834(d, 2H, —CH═C, —ArH), 4.666~4.677(d, 1H, —OH), 3.854(m, 1H, —CHO), 3.541—3.688(m, 7H, six-membered ring intra-CH₂N, amide N six-membered ring outer-CH₂, morpholine 2×—CH₂O), 3.063~3.115(q, 1H, amide N six-membered ring outer-CH₂—), 2.946~2.979(t, 2H, six-membered ring intra-CH₂), 2.394(m, 4H, morpholine-CH₂N, morpholine outer-CH₂N), 2.264~2.278(d, 2H, morpholine-CH₂N), 1.810~1.822(s, 3H, pyrrole-CH₃)

Example 19

(S,Z)-5-(2-Hydroxy-3-morpholin-4-yl-propyl)-2-(5-methoxy-2-oxo-1,2-dihydro-indol-3-ylidenemethyl)-3-methyl-1,5,6,7-tetrahydro-pyrrolo[3,2-c]pyridin-4-one

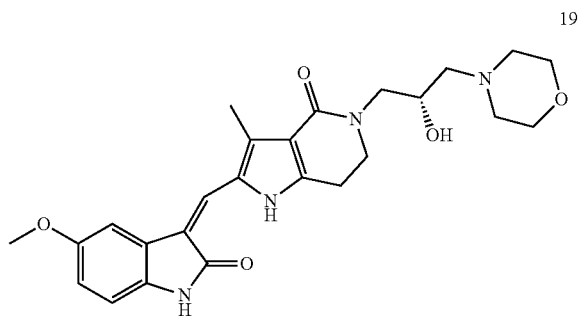

19

The title compound was prepared under the same conditions as described in step 6 of Example 5 with (S)-5-(2-hydroxy-3-morpholin-4-yl-propyl)-3-methyl-4-oxo-4,5,6,7-tetrahydro-1H-pyrrolo[3,2-c]pyridine-2-carbaldehyde 5f obtained from step 5 of Example 5 and 5-methoxy-1,3-dihydro-indol-2-one as starting materials to give (S,Z)-5-(2-hydroxy-3-morpholin-4-yl-propyl)-2-(5-methoxy-2-oxo-1,2-dihydro-indol-3-ylidenemethyl)-3-methyl-1,5,6,7-tetrahydro-pyrrolo[3,2-c]pyridin-4-one 19 (40 mg, yield 76.6%) as a red solid.

MS m/z (ESI): 467.2[M+1]

¹HNMR (400 MHz, DMSO-d6): 13.846 (s, 1H, pyrrole-NH), 10.742 (s, 1H, indole-NH), 7.696(s, 1H, —CH═C), 7.490~7.495(m, 1H, —ArH), 6.728~6.792(m, 2H, —ArH), 4.699~4.711(d, 1H, —OH), 3.896~3.909(m, 1H, —CHO), 3.783(s, 3H, —CH₃O), 3.689~3.732(m, 2H, six-membered ring intra-CH₂N), 3.654(m, 1H, amide N six-membered ring outer-CH₂), 3.558~3.580(t, 4H, morpholine 2×—CH₂O), 3.097~3.150(q, 1 H, amide N six-membered ring outer-CH₂—), 2.978~3.011(t, 2H, six-membered ring intra-CH₂), 2.543(s, 3H, pyrrole-CH₃), 2.414~2.425(m, 4H, morpholine-CH₂N, morpholine outer-CH₂N), 2.299~2.308(m, 2H, morpholine-CH₂N)

Example 20

(S,Z)-2-[4-(2,6-Difluoro-phenyl)-2-oxo-1,2-dihydro-indol-3-ylidenemethyl]-5-(2-hydroxy-3-morpholin-4-yl-propyl)-3-methyl-1,5,6,7-tetrahydro-pyrrolo[3,2-c]pyridin-4-one

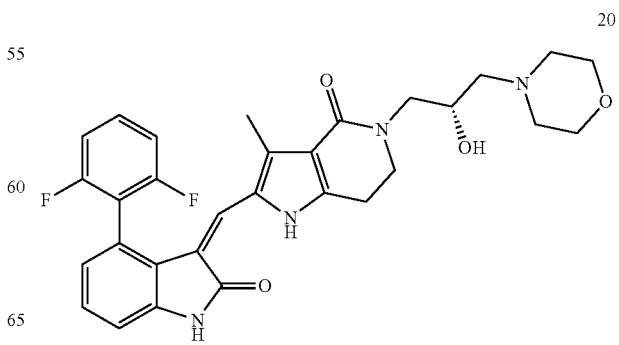

20

The title compound was prepared under the same conditions as described in step 6 of Example 5 with (S)-5-(2-hydroxy-3-morpholin-4-yl-propyl)-3-methyl-4-oxo-4,5,6,7-tetrahydro-1H-pyrrolo[3,2-c]pyridine-2-carbaldehyde 5f obtained from step 5 of Example 5 and 4-(2,6-difluoro-phenyl)-1,3-dihydro-indol-2-one as starting materials to give (S,Z)-2-[4-(2,6-difluoro-phenyl)-2-oxo-1,2-dihydro-indol-3-ylidenemethyl]-5-(2-hydroxy-3-morpholin-4-yl-propyl)-3-methyl-1,5,6,7-tetrahydro-pyrrolo[3,2-c]pyridin-4-one 20 (52 mg, yield 84.7%) as a yellow solid.

MS m/z (ESI): 549.3[M+1]

¹HNMR (400 MHz, DMSO-d6): 13.604(s, 1H, pyrrole-NH), 11.171(s, 1H, indole-NH), 7.646~7.666(m, 1H, —ArH), 7.338~7.380(m, 2H, —ArH), 7.244~7.282(m, 1H, —ArH), 7.008~7.027(m, 1H, —ArH), 6.900~6.919(m, 1H, —ArH), 6.657(s, 1H, —CH═C), 4.672~4.683(d, 1H, —OH), 3.855~3.868(m, 1H, —CHO), 3.541~3.673(m, 7H, six-membered ring intra-CH₂N, amide N six-membered ring outer-CH₂, morpholine 2×—CH₂O), 3.077~3.130(q, 1H, amide N six-membered ring outer-CH₂—), 2.955~2.988(t, 2H, six-membered ring intra-CH₂), 2.394(m, 4H, morpholine-CH₂N, morpholine outer-CH₂N), 2.266~2.280(m, 2H, morpholine-CH₂N), 1.856(s, 3H, pyrrole-CH₃)

Example 21

(S,Z)-5-(2-Hydroxy-3-morpholin-4-yl-propyl)-2-[5-(4-methoxy-phenyl)-2-oxo-1,2-dihydro-indol-3-ylidenemethyl]-3-methyl-1,5,6,7-tetrahydro-pyrrolo[3,2-c]pyridin-4-one

21

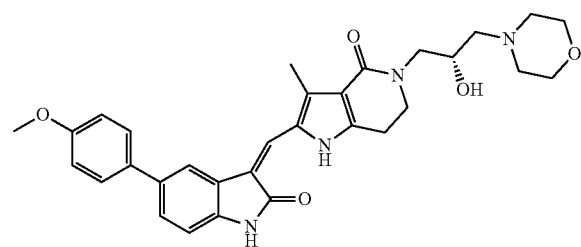

The title compound was prepared under the same conditions as described in step 6 of Example 5 with (S)-5-(2-hydroxy-3-morpholin-4-yl-propyl)-3-methyl-4-oxo-4,5,6,7-tetrahydro-1H-pyrrolo[3,2-c]pyridine-2-carbaldehyde 5f obtained from step 5 of Example 5 and 5-(4-methoxy-phenyl)-1,3-dihydro-indol-2-one as starting materials to give (S,Z)-5-(2-hydroxy-3-morpholin-4-yl-propyl)-2-[5-(4-methoxy-phenyl)-2-oxo-1,2-dihydro-indol-3-ylidenemethyl]-3-methyl-1,5,6,7-tetrahydro-pyrrolo[3,2-c]pyridin-4-one 21 (53 mg, yield 87.2%) as a yellow solid.

MS m/z (ESI): 543.3[M+1]

¹HNMR (400 MHz, DMSO-d6): 13.708(s, 1H, pyrrole-NH), 11.004(s, 1H, indole-NH), 7.321~7.852(m, 1H, —ArH), 7.673(s, 1H, —CH═C), 7.582~7.604(m, 2H, —ArH), 7.254~7.277(m, 1H, —ArH), 7.070(m, 1H, —ArH), 7.016~7.038(d, 2H, —ArH), 4.704~4.716(d, 1H, —OH), 3.855~3.868(m, 1H, —CHO), 3.806(s, 3H, —CH₃O), 3.659~3.728(m, 3H, six-membered ring intra-CH₂N, amide N six-membered ring outer-CH₂), 3.559~3.581(t, 4H, morpholine 2×—CH₂O), 3.077~3.130(q, 1H, amide N six-membered ring outer-CH₂13 ), 2.990~3.024(t, 2H, six-membered ring intra-CH₂), 2.539(s, 3H, pyrrole-CH₃), 2.415~2.427(m, 4H, morpholine-CH₂N, morpholine outer-CH₂N), 2.294~2.311(m, 2H, morpholine-CH₂N)

Example 22

(S,Z)-2-(4-Bromo-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one

22

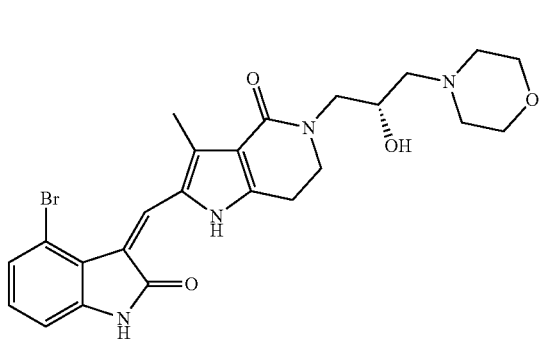

The title compound was prepared under the same conditions as described in step 6 of Example 5 with (S)-5-(2-hydroxy-3-morpholin-4-yl-propyl)-3-methyl-4-oxo-4,5,6,7-tetrahydro-1H-pyrrolo[3,2-c]pyridine-2-carbaldehyde 5f obtained from step 5 of Example 5 and 4-bromo-1,3-dihydro-indol-2-one as starting materials to give (S,Z)-2-(4-bromo-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 22 (43 mg, yield 74.5%) as a yellow solid.

MS m/z (ESI): 515.2[M+1]

¹HNMR (400 MHz, DMSO-d6): 13.670(s, 1 H, pyrrole-NH), 11.189(s, 1H, indole-NH), 8.562(s, 1H, —CH═C), 7.201~7.221(m, 1H, —ArH), 7.042~7.081(m, 1H, —ArH), 6.920~6.938(m, 1H, —ArH), 4.709~4.721(d, 1H, —OH), 3.902~3.915(m, 1H, —CHO), 3.631~3.745(m, 3H, six-membered ring intra-CH₂N, amide N six-membered ring outer-CH₂), 3.558~3.580(t, 4H, morpholine 2×—CH₂O), 3.090~3.143(q, 1H, amide N six-membered ring outer-CH₂—), 3.011~3.035(t, 2H, six-membered ring intra-CH₂), 2.479(s, 3H, pyrrole-CH₃), 2.413~2.426(m, 4H, morpholine-CH₂N, morpholine outer-CH₂N), 2.293~2.311(m, 2H, morpholine-CH₂N)

Example 23

(R,Z)-2-(5-Fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one maleate

23

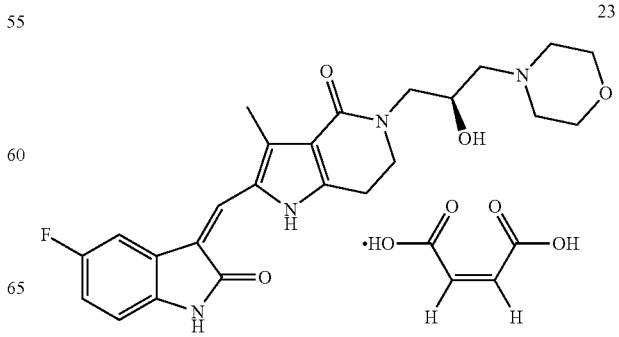

(R,Z)-2-(5-Fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 1 (709 mg, 1.562 mmol) and cis-butenedioic acid (217 mg, 1.874 mmol) were dissolved in 150 mL of methanol under stirring at room temperature. After stirring to mix well, the reaction mixture was heated at 40° C. in an oil bath for 20 minutes and filtered under reduced pressure. The filtrate was concentrated under reduced pressure, and 50 mL of acetonitrile was then added to the residue. Upon completion of the addition, the mixture was heated to reflux for 20 minutes. The reaction mixture was cooled down to room temperature and filtered under reduced pressure to give the title compound (R,Z)-2-(5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one maleate 23 (811 mg, yield 91.1%) as a yellow solid.

MS m/z (ESI): 455.2[M+1]

Example 24

(R,Z)-2-(5-Fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one malate

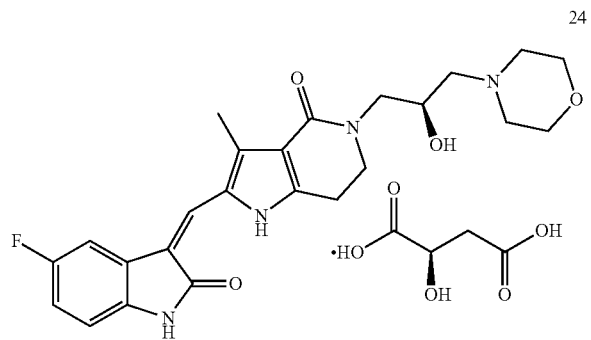

24

2-Hydroxy-succinic acid (231 mg, 1.72 mmol) was dissolved in 100 mL of methanol under stirring at room temperature, and (R,Z)-2-(5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one 1 (560 mg, 1.233 mmol), 200 mL of methanol and 100 mL of water was then added to the solution in batch. Upon completion of the addition, the reaction system was heated at 50° C. in an oil bath in dark until a clear solution was obtained. The reaction mixture was filtered and the filtrate was concentrated under reduced pressure to remove the solvent to give a yellow solid. The resulting solid was dissolved in 100 mL of acetonitrile, and the mixture was heated to reflux in dark for 1.5 hours. The oil bath was removed. The reaction system was naturally cooled down to room temperature and filtered to give the title compound (R,Z)-2-(5-fluoro-2-oxo-1,2-dihydro-indol-3-ylidenemethyl)-5-(2-hydroxy-3-morpholin-4-yl-propyl)-3-methyl-1,5,6,7-tetrahydro-pyrrolo[3,2-c]pyridin-4-one malate 24 (718 mg, yield 99%) as a yellow solid.

MS m/z (ESI): 455.2[M+1]

Biological Assays

Example 1

Cell Proliferation Inhibition Assay

The following in vitro assay could be used to determine the level of activity and effect of different compounds of this invention through a proliferation inhibition experiment (cell toxicity) on Homo sapiens HUVEC cell, which has high expression of VEGFR.

The cellular assay described here is used to test anti-angiogenesis and proliferation inhibition activity and effect of the compounds through VEGFR on the cancer cells in vitro. The effect and activity is represented by the $IC_{50}$ value that kills the cancer cells. The general procedures of the assay are as follows: The Homo sapiens cells that highly expressing VEGFR were chosen and seeded to 96-well cell culture plate at a suitable concentration (e.g., 5000 cells/mL medium). The cells then were incubated in carbon dioxide ($CO_2$) incubator until they reached 85% confluency. Then, the cell culture medium was replaced by fresh one with testing compounds added in it at serial concentrations (general 6 or 7 concentrations). Then the cells were put back to the incubator and cultured for 72 hours continuously. 72 hours later, the treated compounds were assayed for their proliferation status by using Sulforhodamine B (SRB) method. $IC_{50}$ of compounds on tested cells was calculated by using data of inhibition rate of serial concentrations of the testing compounds.

Material and Methods a. Dimethyl sulfoxide (Sinophma chemical reagent company, catalog No. T20050806)
b. HUVEC cells (Purchased from Institute of biochemistry and cell biology)
c. Falcon 100 mm cell culture plate (Baton Dickison Labware, Baton Dickison and company, Catalog No. 18677)
d. Corning 96-well culture cluster (Corning Incorporated, Catalog No. 3599)
e. Fisher Pipette (Fisher scientific, Catalog No. 03-692-164)
f. DMEM/F12 cell medium (Gibco, Catalog No. 12400-024)
g. Fetal bovine serum, Australia origin (Gibco, Catalog No. 10099-141)
h. Phosphate Buffered Saline (Gibco, Catalog No. 10010-072)
i. 0.25% Trypsin-EDTA (Gibco, Catalog No. 25200-056)
j. Sulforhodamine B (Sigma, Catalog No. 3520-42-1)
k. Acetic Acid (Sinophma chemical reagent company, Catalog No. T20060508)
l. Trichloroacetic Acid (Sinophma chemical reagent company, Catalog No. T20060305)
m. Tris base (Amresco, Catalog No. 0826)
n. Class II A/B3 Biological safety cabinet (ThermoForma, Catalog No. HB0053-03)
o. Series II water jacketed $CO_2$ incubator (ThermoForma, Model 3111)
p. Centrifuge (Fisher Scientific Marathon 8 k, Catalog No. 0027-02)
q. Novastar Plate reader (BMG Labtech, Catalog No. 700-0081)
r. Orbital Shaker (Qilinbeier, Catalog No. TS-1)

Protocol

The following protocol is used to assay the cell toxicity (anti-proliferation activity, which is expressed as $IC_{50}$ value) of testing compounds of the invention on HUVEC cell:

1. HUVEC cells were cultured with growth media (DMEM/F12, supplemented with 10% FBS) in 100 mm corning culture plate at 37° C., 5% $CO_2$ till confluency.
2. HUVEC cells were washed with cold PBS solution, then the cells were harvested by trypsinization and seeded in corning 96-well cell culture plates at a concentration of 50,000 cells/ml, 6 empty wells were left on each plate as plate background.
3. The cells were cultured in 96-well plates at 37° C., 5% $CO_2$, till 85% confluency.

4. The compound stock solution was prepared by using DMSO to solve candidate compounds to a concentration of 20 mM. Then DMSO was used to dilute the stock solution to a serial concentration to prepare testing compound solution samples (e.g., 2 mM, 1 mM, 0.2 mM, 20 μM, 2 μM, 0.2 μM).
5. Cell culture medium (DMEM/F12+10% FBS) was used to dilute the compound solution prepared previously. Each concentration of testing compound solution was diluted by 20 times by adding 5 μl DMSO compound solution to 95 μl culture medium, and then mixed thoughtfully by vortex. This would ensure that the final DMSO concentration in the HUVEC cell culture medium was less than 0.5%.
6. After HUVEC cell had attached to dish bottom and reached 85% confluency, the culture medium was replaced with fresh DMEM/F12 medium plus 10% FBS. 180 μl medium was added to each well, then 20 μl diluted testing compound solution prepared in step 5 was added. For negative control group cells, 20 μl culture medium containing 0.5% pure DMSO was added for instead. That is, HUVEC cells were exposed to each testing compound in a final concentration of 100 μM, 10 μM, 5 μM, 0.1 μM, 0.01 μM, and 0.001 μM.
7. The culture plates were put back to incubator and cultured for 72 hours at 37° C., 5% $CO_2$.
8. 72 hours later, culture plates were transferred from incubator to sterile work area.
9. Fixing solution (50% Trichloroacetic Acid, TCA) was prepared by adding reagent grade water to the TCA; fixing the cells by gently layering 50 μl of cold TCA solution on top of the growth medium.
10. The plates were incubated at 4° C. for 1 hour, and then rinsed with distilled water for several times to remove TCA, serum proteins and etc. Plates were air dried and stored at 4° C. until use. Background absorbance was measured in wells incubated only with growth medium.
11. 0.4% Sulforhodamine B solution was prepared by using 10% acetic acid solution. 50 μl Sulforhodamine B solution was added to each well of 96-well plates.
12. The cells were allowed to be stained for 30 minutes.
13. The 10% acetic acid washing solution was prepared. At the end of the staining, the staining solution was discarded, and the cells were rinsed quickly with 10% acetic acid. The above operation was repeated until unincorporated dye was removed. Washing times were kept in minimum in order to reduce desorption of protein-bound dye. After being rinsed, the cultures were air dried.
14. The incorporated dye was then dissolved in a volume of Sulforhodamine B. Solubilization solution (10 mM Tris), which was equal to the original volume of culture medium (normally 200 uL). All cultures were incubated for 5 minutes at room temperature on orbital shaker to accelerate dissolving process.
15. The absorbance was measured by spectrophotometry at a wavelength of 565 nm. The background absorbance of 96-well plates at 690 nm was measured and subtracted from the measurement at 565 nm.
16. The inhibition rate (IR) was calculated as follows:
    IR=100×(Absorbance of control cells−Absorbance of cells exposed to compound at each concentration)/Absorbance of control cells %.
    The $IC_{50}$ value can be calculated from the IRs of compounds at different concentration gradients.

The Activity of the Compounds of the Invention

The biological activity of the compounds of the invention is tested using the assay described above. The $IC_{50}$ values are calculated and showed in table below:

| Example No. | $IC_{50}$ (VEGFR/HUVEC)(μM) |
|---|---|
| 1 | 0.027 |
| 2 | 2.4 |
| 3 | 0.84 |
| 5 | 0.012 |
| 20 | 0.01 |

Example 2

VEGF-R2 Kinase Assay

This assay is used to measure the in vitro kinase activity of recombinant human VEGF-R2 in an enzyme-linked immunosorbent assay (ELISA).

Materials and Reagents a. Washing Buffer (PBS-T Buffer): 1×PBS (137 mM NaCl, 2.7 mM KCl, 4.3 mM $Na_2HPO_4$, 1.4 mM $KH_2PO_4$, pH 7.2) plus 0.05% Tween-20.
b. 1% Bovine Serum Albumin (BSA, Calbiochem #136593) in PBS-T Buffer.
c. Stopping solution: 50 mM EDTA, pH 8.0.
d. DELFIA® Europium-labeled Anti-mouse IgG (PerkinElmer Life Sciences #AD0124).
e. DELFIA® Enhancement Solution (PerkinElmer Life Sciences #1244-105).
f. DELFIA® Streptavidin coated, 96-well, yellow plate (PerkinElmer Life Sciences #AAAND-0005).
g. Recombinant human VEGFR-2 kinase (supplied in 50 mM Tris-HCl, pH8.0, 100 mM NaCl, 5 mM DTT, 15 mM reduced glutathione and 20% glycerol). (Cell signaling technology #7787).
h. 10 mM ATP solution (Cell signaling technology #9804).
i. Biotin-Gastrin Precursor (Tyr87) Peptide (Cell signaling technology #1310).
j. Phospho-Tyrosine Mouse mAb (P-Tyr-100) (Cell signaling technology #9411).
k. HTScan™ Tyrosine Kinase Buffer (4×).
   1× Kinase Buffer:
   60 mM HEPES
   5 mM $MgCl_2$
   5 mM $MnCl_2$
   3 μM $Na_3VO_4$
l. 1.25M DTT (1000×) (Cell signaling technology).

Procedure

The following protocol was used:
1. The testing compounds were diluted with DMSO to desired final concentration. 1 μl of the testing compound, the negative control and the blank control (the assay of negative control and the blank control which did not contain any test compound) were added for each assay.
2. 6 μM peptide substrate (Tyr87) was diluted with d.$H_2O$ in a ratio of 1:1; 15 μl was added to each assay.
3. VEGFR-2 kinase was transferred from −80° C. to ice immediately, and the kinase was thawed on ice.
4. 2.2 μs VEGFR-2 enzyme was added to enzyme tube.
5. 10 μl of DTT (1.25M) was added to 2.5 ml of 4× HTScan™ Tyrosine Kinase Buffer (240 mM HEPES, pH 7.5, 20 mM $MgCl_2$, 20 mM $MnCl_2$, 12 μM $Na_3VO_4$) to prepare DTT/Kinase buffer.
6. 0.75 ml of DTT/Kinase buffer was transferred to the enzyme tube to prepare 4× reaction cocktail, and 7.5 μl 4× reaction cocktail was added to each assay.

7. 2 μl ATP (10 mM) was added to 498 μl dH$_2$O, and 7.5 μl was added to each assay. Final Assay Conditions for a 30 μl Reaction system
60 mM HEPES pH 7.5
5 mM MgCl$_2$
5 mM MnCl$_2$
3 μM Na$_3$VO$_4$
1.25 mM DTT
10 μl M ATP
1.5 μM substrate peptide
22ng VEGFR-2 Kinase
8. The reaction tube was incubated at 25° C. for 30 minutes.
9. 30 μl/assay stopping solution (50 mM EDTA, pH 8.0) was added to stop the reaction.
10. 25 μl of each reaction and 75 μl dH$_2$O were transferred to a 96-well streptavidin coated plate, with shaking at room temperature for 60 minutes.
11. Each well was washed for three times with 200 μl PBS-T buffer. Plate was patted on paper towel to remove excess liquid.
12. Primary antibody, Phospho-Tyrosine mAb (P-Tyr-100) was diluted in a ratio of 1:1000 with PBS-T buffer which contains 1% BSA, and 100 μl diluted primary antibody was added to each well.
13. The plate was incubated with shaking at room temperature for 60 minutes.
14. Washing step was carried out as described in step 11.
15. Europium labeled anti-mouse IgG was diluted in a ratio of 1:500 with PBS-T buffer which contains 1% BSA. 100 μl diluted antibody was added to each well.
16. The plate was incubated with shaking at room temperature for 30 minutes.
17. Each well was washed for five times with 200 μl PBS-T buffer. Plate was patted on paper towel to remove excess liquid.
18. 100 μl DELFIA® Enhancement Solution was added to each well.
19. The plate was incubated with shaking at room temperature for 5 minutes.
20. The fluorescence intensity was detected at wavelength of 615 nm in a time-resolved fluorescence mode on plate reader.

Calculate inhibition rate:
IR (%)=100−100*(X−B)/(N−B)
X=Fluorescence value of the well contained testing compound
N=Fluorescence value of the positive control
B=Blank
The IC$_{50}$ value can be calculated from the IRs of compounds at different concentration gradients.

The Activity of the Compounds of the Invention

The biochemical activity of the compounds of the invention is tested using the assay described above. The IC$_{50}$ values are measured and showed in table below:

| Example No. | IC$_{50}$ (VEGFR/bio)(μM) |
|---|---|
| 1 | 0.001 |
| 4 | 0.998 |
| 11 | 0.003 |
| 13 | 0.13 |
| 16 | 0.11 |
| 17 | 0.004 |

What is claimed is:

1. A compound according to formula (I) or a pharmaceutically acceptable salt thereof:

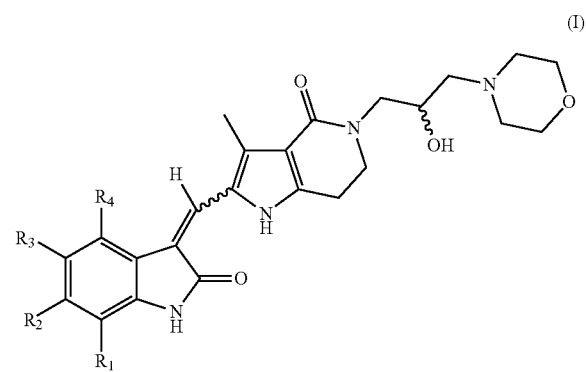

(I)

wherein:
R$_1$, R$_2$, R$_3$, R$_4$ are each independently selected from the group consisting of hydrogen, halogen, alkyl, aryl, heteroaryl, —OR$_5$, —O[CH$_2$CH$_2$O]$_r$R$_7$, —NR$_5$R$_6$, —COR$_5$ and —NR$_5$COR$_6$, wherein said aryl or heteroaryl is further substituted by one or more groups selected from the group consisting of alkyl, alkoxyl and halogen;

R$_5$ and R$_6$ are each independently selected from the group consisting of hydrogen and alkyl, wherein said alkyl is further substituted by one or more groups selected from the group consisting of aryl, heteroaryl, haloaryl, hydroxyl, alkoxyl, aryloxyl, carboxylic acid and carboxylic ester;

R$_7$ is hydrogen or alkyl; and
r is an integer from 1 to 6.

2. A compound or a pharmaceutically acceptable salt thereof according to claim 1, selected from the group consisting of:

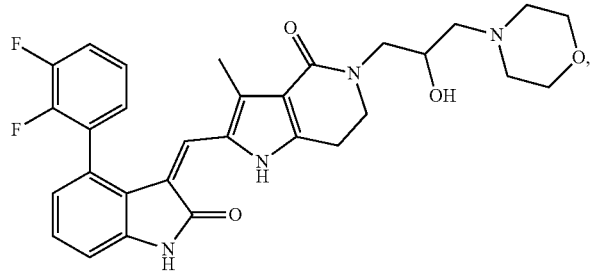

-continued
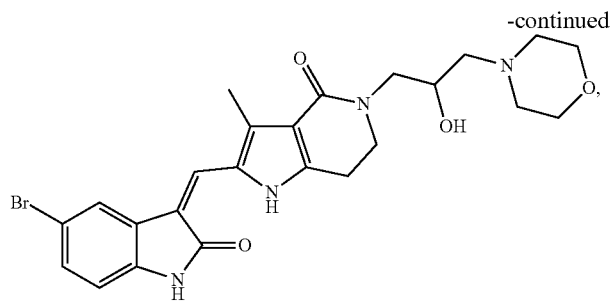
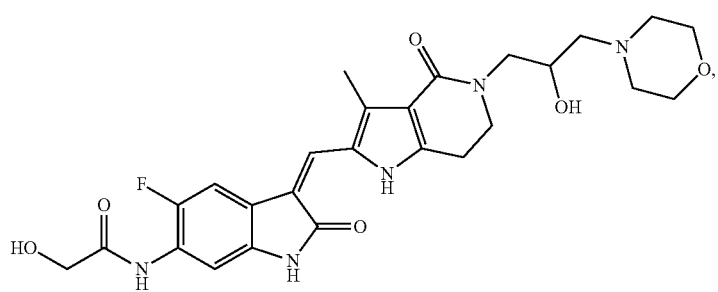
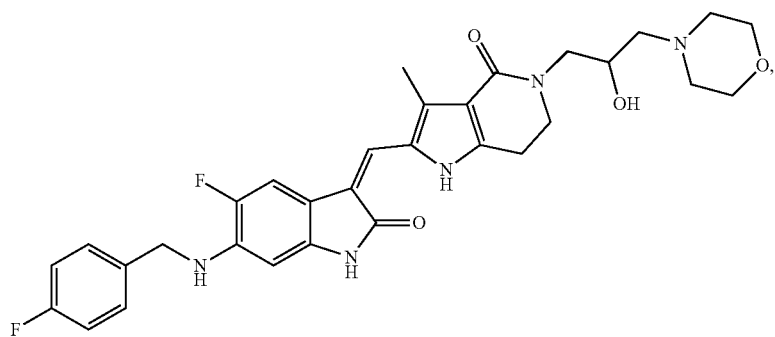
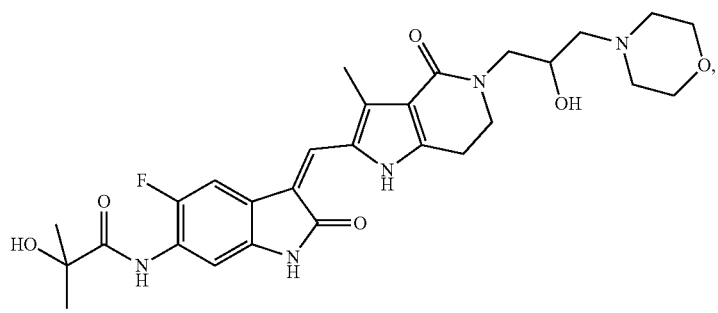
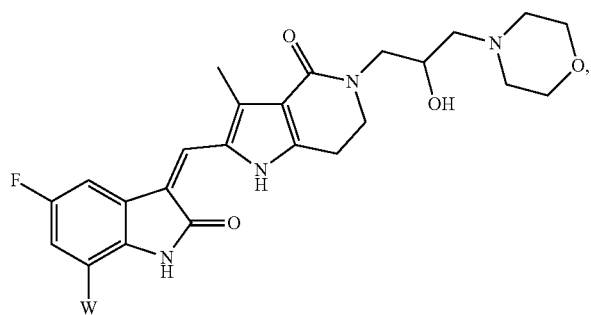

-continued
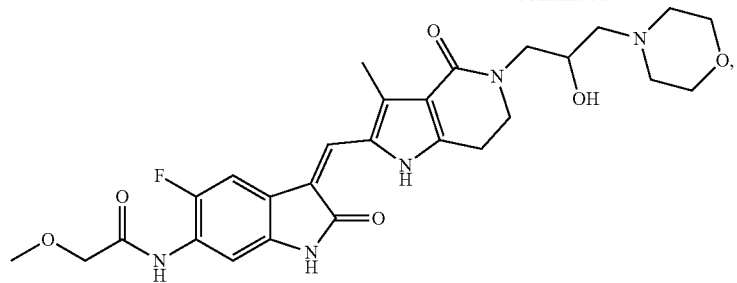
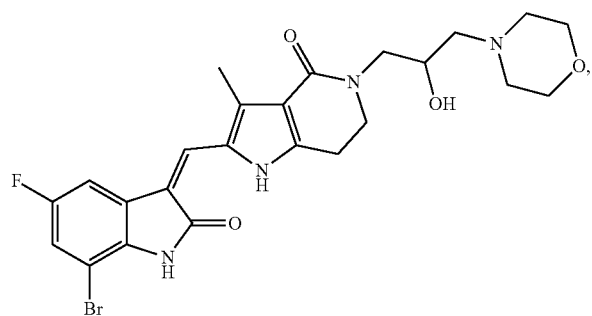
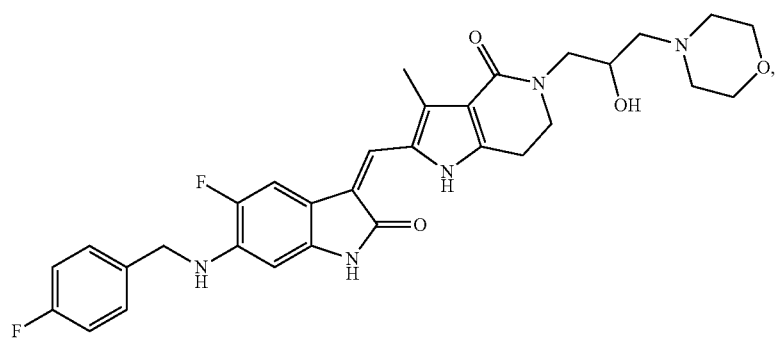
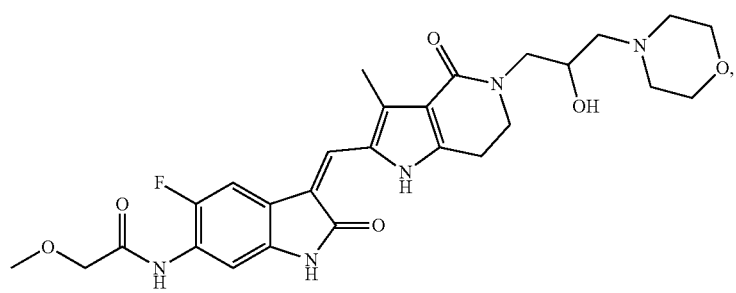
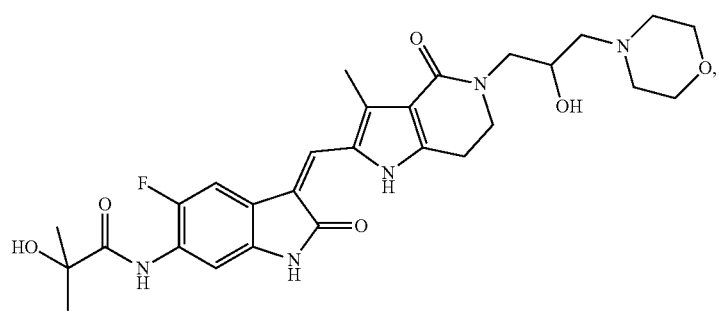

-continued
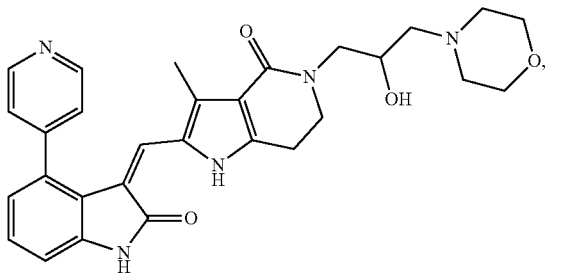
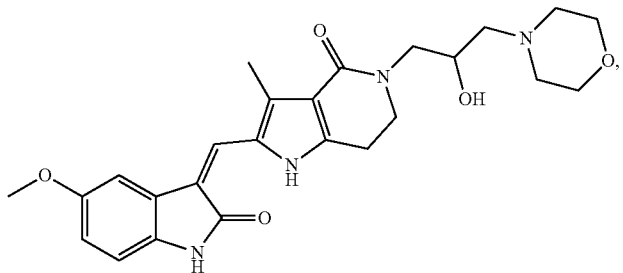
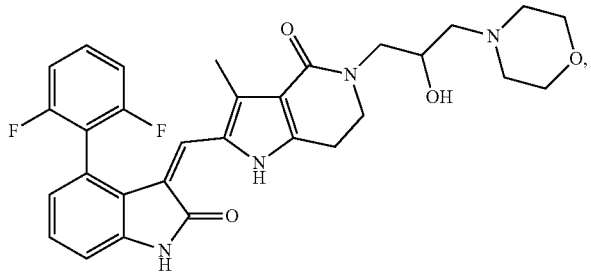
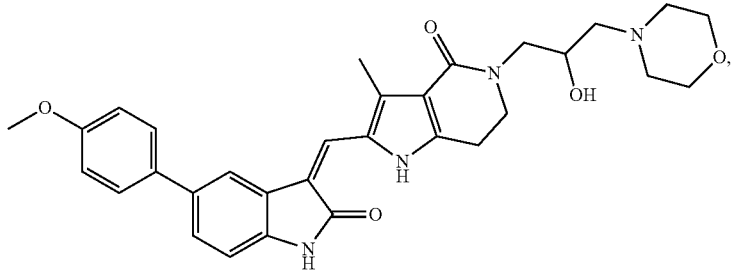
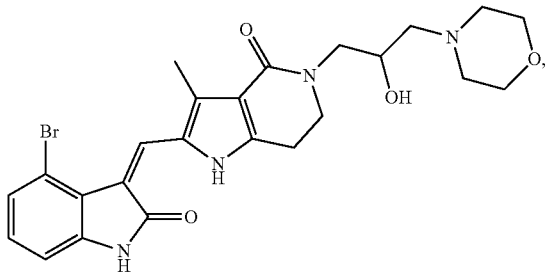
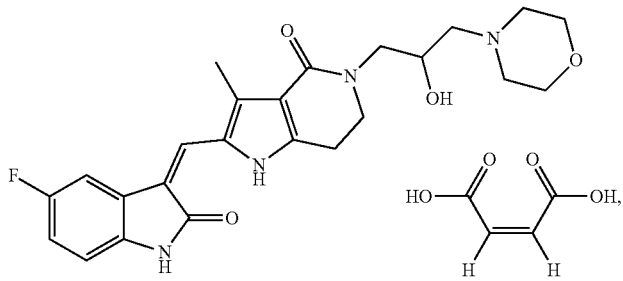 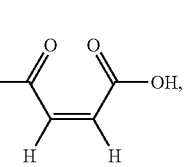 and

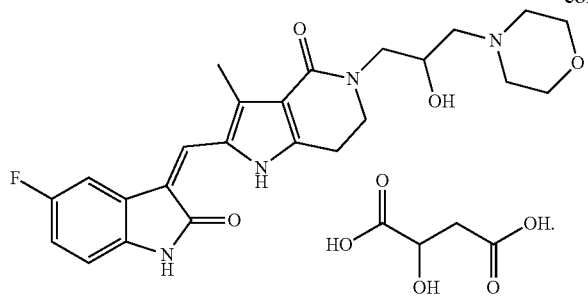

3. A pharmaceutical composition comprising a compound, or a pharmaceutically acceptable salt thereof, according to any one of claims 1 or 2, in an effective therapeutic dose as well as a pharmaceutically acceptable carrier.

4. A compound or a pharmaceutically acceptable salt thereof according to claim 1, wherein the said pharmaceutically acceptable salt is a salt formed with said compound and an acid selected from the group consisting of malic acid, lactic acid, maleic acid, hydrochloric acid, methanesulfonic acid, sulfuric acid, phosphoric acid, citric acid, tartaric acid, acetic acid and trifluoroacetic acid.

5. A compound or a pharmaceutically acceptable salt thereof according to claim 4, wherein the said acid is malic acid or maleic acid.

6. A preparation process of the compound or a pharmaceutically acceptable salt thereof according to claim 1, comprising the following steps of:

heating the optically active compound of 1-amino-3-morpholin-4-yl-propan-2-ol (Ia) with 5-carboxymethyl-3-methyl-1H-pyrrole-2,4-dicarboxylic acid 2-tent-butyl ester 4-ethyl ester in acetonitrile in the presence of 1-hydroxybenzotriazol and N-ethyl-N'-(dimethylaminopropyl)-carbodiimide to obtain chiral pyrrole amide dicarboxylic acid diester (Ib) under a nitrogen atmosphere;

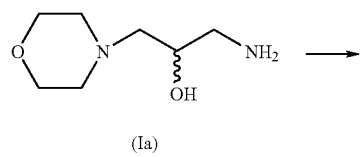

(Ia)

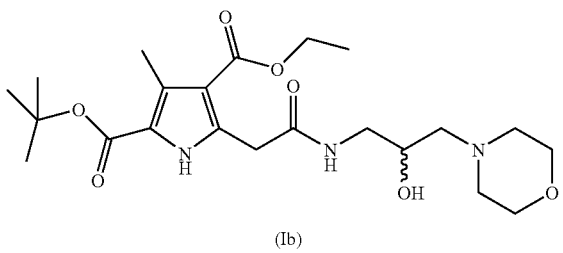

(Ib)

heating chiral pyrrole amide dicarboxylic acid diester (Ib) with hydrochloric acid to reflux in ethanol to obtain optically active pyrrole amide ethyl ester (Ic) under an argon atmosphere;

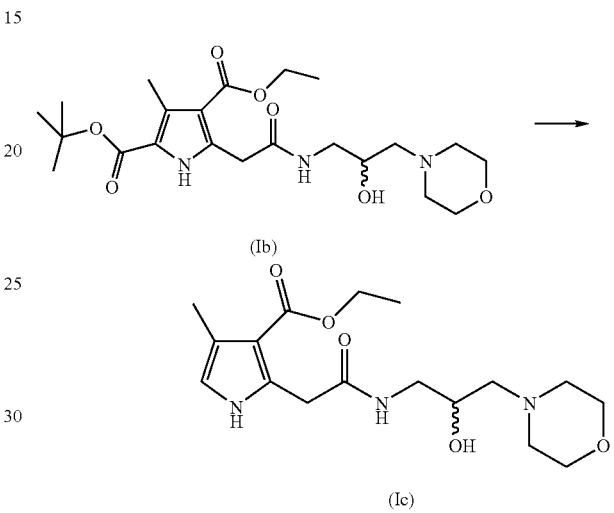

further, heating optically active pyrrole amide ethyl ester (Ic) with borane to reflux in anhydrous tetrahydrofuran by selective reduction to obtain chirally substituted pyrrole ethyl ester (Id);

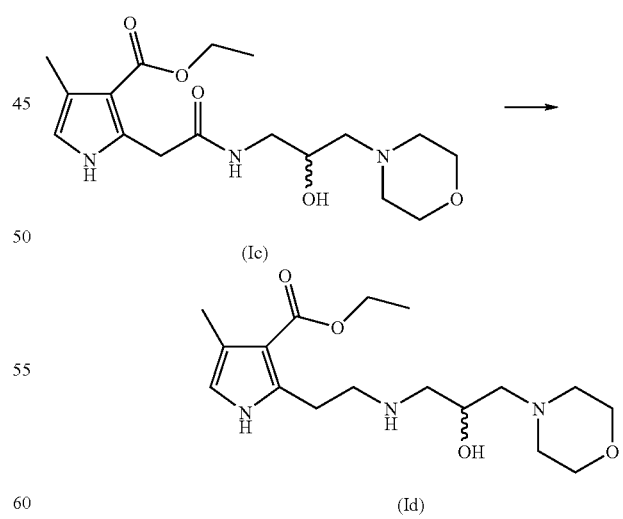

and then, heating chirally substituted pyrrole ethyl ester (Id) with lithium hydroxide monohydrate to reflux in glycol to obtain the cyclized product of optically active pyrrolofused six-membered aza-heterocycle (Ie) under an argon atmosphere;

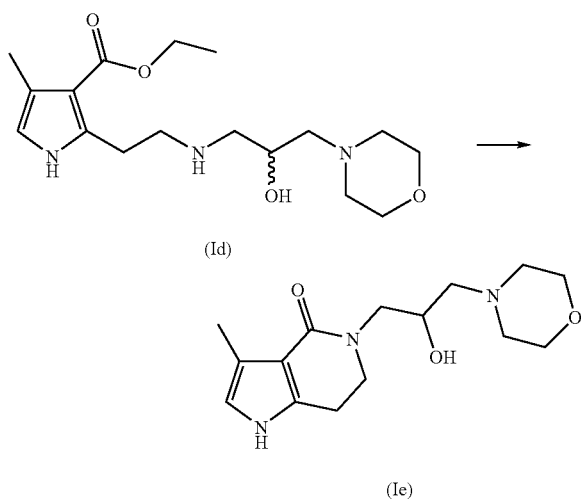

(Id)

(Ie)

reacting optically active pyrrolofused six-membered aza-heterocycle (Ie) with phosphorus oxychloride and N,N-dimethylformamide in anhydrous dichloromethane at room temperature by formylation reaction to obtain optically active pyrrolofused six-membered aza-heterocyclic formaldehyde (If);

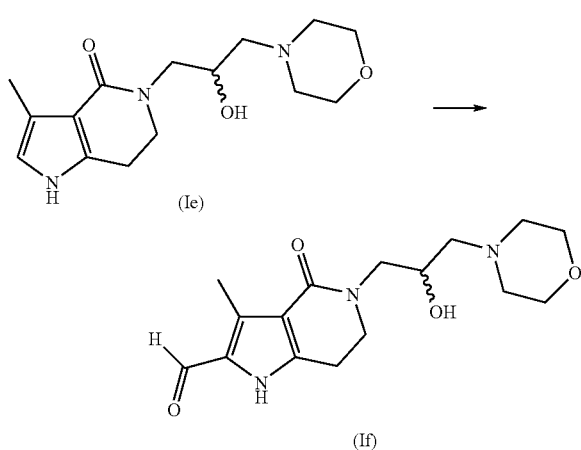

(Ie)

(If)

finally, heating optically active pyrrolofused six-membered aza-heterocyclic formaldehyde (If) with different indolinones in the presence of a base such as triethylamine or piperidine for 2~12 hours to obtain a compound of of formula (I);

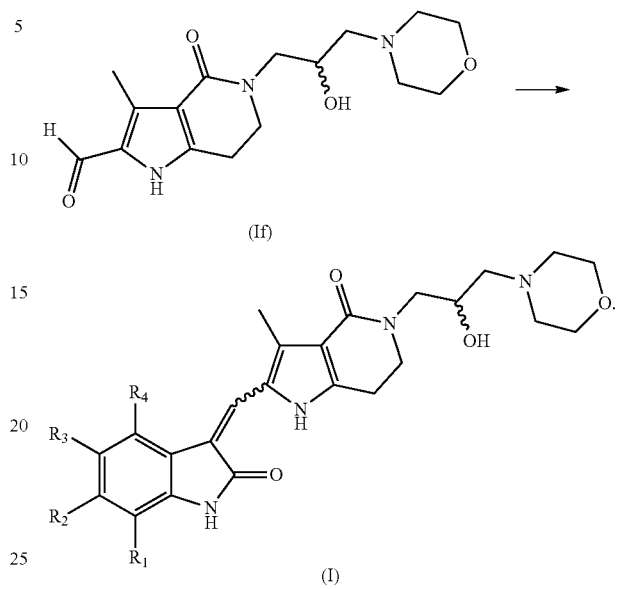

(If)

(I)

7. A method for modulating the catalytic activity of a protein kinase, comprising a step of contacting said protein kinase with said compound or pharmaceutically acceptable salt thereof according to anyone of claims 1 to 5.

8. A method according to claim 7, wherein said protein kinase is selected from the group consisting of receptor tyrosine kinase (RTK), nonreceptor protein tyrosine kinase (CTK) and serine/threonine protein kinase (STK).

9. A method of treating a protein kinase related disorder which comprises a step of administering to a patient in need thereof, a therapeutically effective amount of a compound or a pharmaceutically acceptable salt thereof according to claim 1.

10. A method according to claim 9, wherein the said protein kinase related disorder is selected from disorder related to VEGFR-2, EGFR, HER-2, HER-3, HER-4, PDGFR, c-Kit, c-Met, FGFR and Flt3.

11. A method for modulating the catalytic activity of a protein kinase, comprising a step of contacting said protein kinase with said pharmaceutical composition according to claim 3.

* * * * *